US006495330B1

(12) United States Patent
Rademacher et al.

(10) Patent No.: US 6,495,330 B1
(45) Date of Patent: Dec. 17, 2002

(54) MATERIALS AND METHODS RELATING TO THE DIAGNOSIS AND TREATMENT OF PRE-ECLAMPSIA AND DIABETES

(75) Inventors: Thomas William Rademacher, Oxford; Patricia McLean, Surrey, both of (GB)

(73) Assignee: Rodaris Pharmaceuticals Limited, Oxford (GB)

( * ) Notice: Subject to any disclaimer, the term of this patent is extended or adjusted under 35 U.S.C. 154(b) by 0 days.

(21) Appl. No.: 09/254,745

(22) PCT Filed: Sep. 11, 1997

(86) PCT No.: PCT/GB97/02534

§ 371 (c)(1),
(2), (4) Date: Jun. 4, 1999

(87) PCT Pub. No.: WO98/10791

PCT Pub. Date: Mar. 19, 1998

(30) Foreign Application Priority Data

Sep. 11, 1996 (GB) .............................................. 9618931

(51) Int. Cl.[7] .............................................. G01N 33/53

(52) U.S. Cl. .............................. 435/7.1; 435/4; 436/501

(58) Field of Search ........................ 435/4, 71; 436/501

(56) References Cited

FOREIGN PATENT DOCUMENTS

EP 0412700 * 7/1990

OTHER PUBLICATIONS

Farese et al. PNAS.USA. vol. 91: 11040–11044, 1994.*
The Merck Manual of Diagnosis and Therapy, Merck Research Laboratories 17th Ed, p. 2057, 1999.*
Arkwright, P. et al., "Pre–Eclampsia Is Associated with an Increase In Trophoblast Glycogen Content and Glycogen Synthase Activity, Similar to that Found in Hydatiform Moles," 91 *J. Clin. Invest.* 2744–2753 (1993).
Asplin, I. et al., "chiro–Inositol Deficiency and Insulin Resistance: A Comparison of the chiro–Inositol– and the myo–Inositol–Containing Insulin Mediators Isolated From Urine, Hemodialysate, and Muscle of Control and Type II Diabetic Subjects," 90 *Proc. Natl. Acad. Sci. USA* 5924–5928 (1993).
Barash, V. et al., "Mechanism of Placental Glycogen Deposition in Diabetes in the Rat," 24 *Diabetologia* 63–68 (1983).
Bruni, P. et al., "An Inositol Phosphoglycan Stimulates Glycolysis in Human Platelets," 180 *Biochem. Biophys. Res. Commun.* 1041–1047 (1991).
Diamant, Y. et al., "Activity of Placental Enzymes of Carbohydrate and Lipid Metabolism in Normal, Toxemic and Small–For–Date Pregnancies," 12 *Isr. J. Med. Sci.* 243–247 (1976).

Diamant, Y. et al., "Enzymes of Glucose and Fatty Acid Metabolism in Early and Term Human Placenta," 121 *Amer. J. Obstet. Gynecol.* 58–61 (1975).
Fanjul, L. et al., "Follicle–Stimulating Hormone and Human Chorionic Gonadotrophin Induced Changes in Granulosa Cell Glycosyl–Phosphatidylinositol Concentration," 155 *J. Cell. Physiol.* 273–281 (1993).
Igarashi, Y., and Chambaz, E., "A Novel Inositol Glycophospholipid (IGPL) and the Serum Dependence o Its Metabolism in Bovine Adrenocortical Cells," 145 *Biochem Biophys. Res. Commun.* 249–256 (1987).
Kaaja, R. et al., "Serum Lipoproteins, Insulin and Urinary Prostanoid Metabolites in Normal and Hypertensive Pregnant Women," 85 *Obstet. Gynecol.* 353–356 (1995).
Kojima, I. et al., "Insulin–Like Growth Factor–I Stimulates Diacylglycerol Production Via Multiple Pathways in Balb/c 3T3 Cells," 265 *J. Biol. Chem.* 16846–16850 (1990).
Kunjara, S. et al., "Tissue Specific Release of Inositol Phosphoglycans," In *Biopolymers and Bioproducts: Structure, Function, and Applications,* Svasti, J. et. al. (Eds). Bangkok, Thailand. Samakkhisan (Dokya). Public Co. Ltd. 301–306 (1995).
Larner, J. et al., "Insulin Mediators and the Control of Pyruvate Dehydrogenase Complex," 573 *Annals N.Y. Acad. Sci.* 297–305 (1989).
Lazar, D. et al., "Stimulation of Glycogen Synthesis By Insulin in Human Erythroleukemia Cells Requires the Synthesis of Glycosyl–Phosphatidyl Inositol," 91 *Proc. Natl. Acad. Sci. USA* 9665–9669 (1994).
Lilley, K. et al. "Insulin Mediator Stimulation of Pyruvate Dehydrogenase Phosphatase," 296 *Arch. Biochem. Biophys.* 170–174 (1992).
Martiny, L. et al., "Control By Thyrotropin of the Production By Thyroid Cells of an Inositol Phosphate–Glycan," 2 *Cell Signalling* 21–27 (1990).
Nestler, J. et al., "Insulin Mediators are the Signal Transduction System Responsible for Insulin Action on Human Placental Steroidogenesis," 129 *Endocrinology* 2951–2956 (1991).
Newman, J. et al., "Assay of Insulin Mediator Activity with Soluble Pyruvate Dehydrogenase Phosphatase," 116 *Endocrinology* 1912–1919 (1985).
Rademacher, T. et al., "Inositolphosphoglycan Second Messengers," 27 *Brazilian J. Med. Biol. Res.* 327–341 (1994).
Redline, R., and Petterson, P. "Pre–Eclampsia is Associated with an Excess of Proliferative Immature Intermediate Trophoblast," 26 *Human Pathol.* 594–600 (1995).

(List continued on next page.)

*Primary Examiner*—Patrick J. Nolan
(74) *Attorney, Agent, or Firm*—Emily M. Haliday; Quine Intellectual Property Law Group, P.C.

(57) ABSTRACT

The present invention relates to materials and methods for the diagnosis and treatment of pre-eclampsia, and more particularly to the role of P-type inositolphosphoglycans (IPGs) in the occurrence of pre-eclampsia. Methods of diagnosing pre-eclampsia by determining the level of P-type IPGs and uses of antagonists of P-type IPGs in the treatment of pre-eclampsia are disclosed, together with a method for screening for P-type IPG antagonists.

18 Claims, 11 Drawing Sheets

OTHER PUBLICATIONS

Redman, C., "Current Topic: Pre–Eclampsia and the Placenta," 12 *Placenta* 301–308 (1991).

Roberts, J. et al, "Pre–Eclampsia: An Endothelial Cell Disorder," 161 *Am. J. Obstet. Gynecol.* 1200–1204 (1989).

Robertson, W. et al., "The Pathological Response of the Vessels of the Placental Bed to Hypertensive Pregnancy," 93 *J. Path. Bacteriol.* 581–592 (1967).

Rodbell, M., "Metabolism of Isolated Fat Cells," 239 *J. Biol. Chem.* 375–380 (1964).

Romero, G., "Inositolglycans and Cellular Signalling," 15 *Cell Biol. International Rep.* 827–852 (1991).

Romero, G. and Larner, J., "Insulin Mediators and the Mechanism of Insulin Action," 24 *Adv. Pharmacol.* 21–50 (1993).

Romero, G. et al., "The Involvement of Inositol Phosphoglycan Mediators in the Modulation of Steroidogenesis by Insulin and Insulin–Like Growth Factor–I,". 132 *Endocrinology* 1561–1568 (1993).

Shafrir, E. and Diamant, Y., "Regulation of Placental Enzymes of the Carbohydrate and Lipid Metabolic Pathways," 63 *Ciba Foundation Symposium* 161–179 (1978).

Shafrir, E. and Barash, V., "Placental Glycogen Metabolism in Diabetic Pregnancy," 27 *Isr. J. Med. Sci.* 449–461 (1991).

Sochor, M. et al., "Glucose Over– and Under–Utilization in Diabetes: Comparative Studies in Changes of Activities of Enzymes of Glucose Metabolism in Rat Kidney and Liver," 7 *Molecular Physiol.* 51–67 (1985).

Suzuki, S. et al., "Partial Purification Form Human Mononuclear Cells and Placental Membranes of an Insulin Mediator Which Stimulates Pyruvate Dehydrogenase and Suppresses Glucose 6–Phosphatase," 235 *Arch. Biochem. Biophys.* 418–426 (1984).

Vivien, D. et al., "IPG (Inositolphosphate Glycan) as a Cellular Signal for TGF–$\beta$1 Modulation of Chondrocyte Cell Cycle," 155 *J. Cellular Physiol.* 437–444 (1993).

Caro et al. Biochemical and Molecular Medicine, vol. 61, pp. 214–228, 1007.*

Galasko et al. J. of Clinical Endocrinology and Metabolism, vol. 80, pp. 2419–2429, 1995.*

* cited by examiner

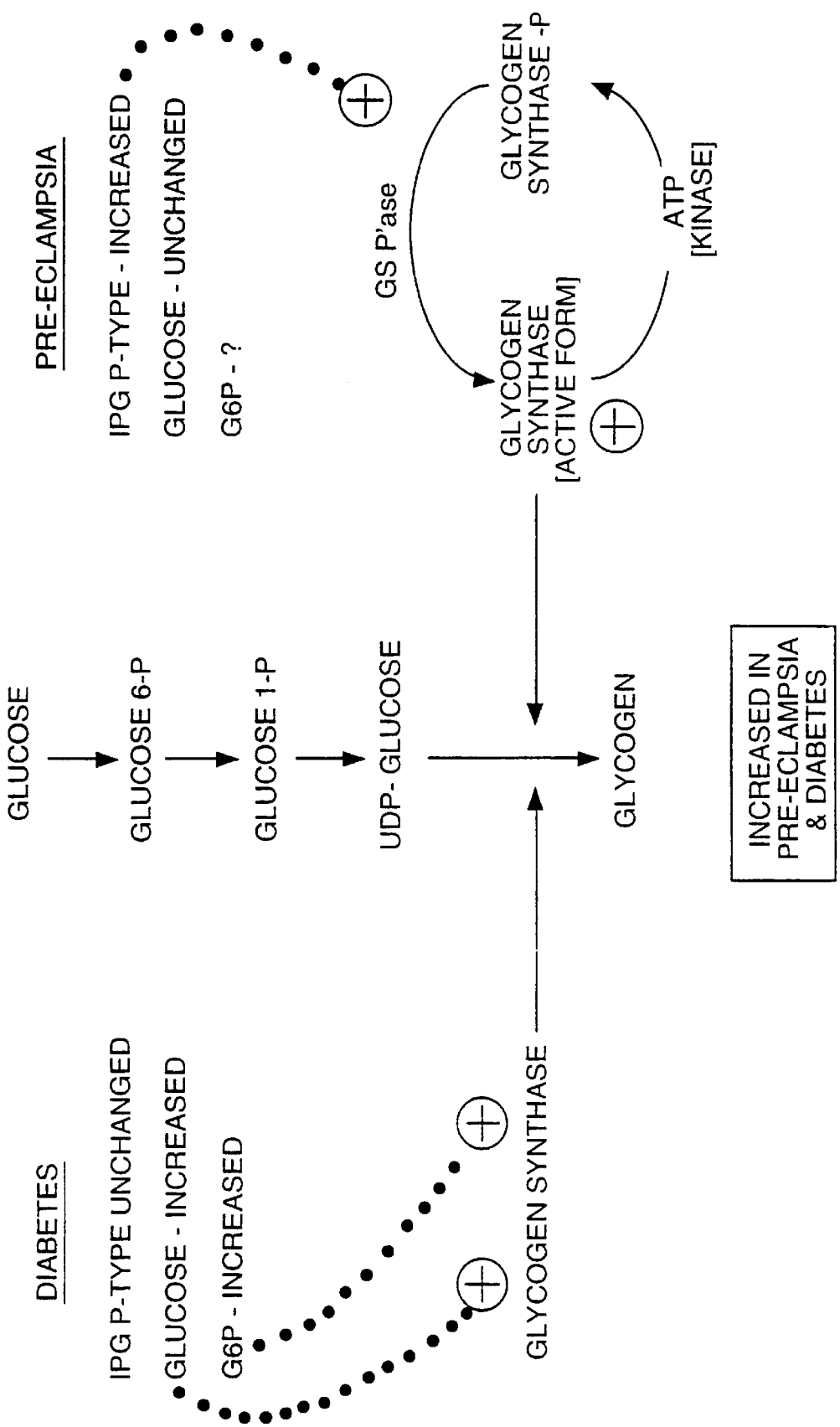

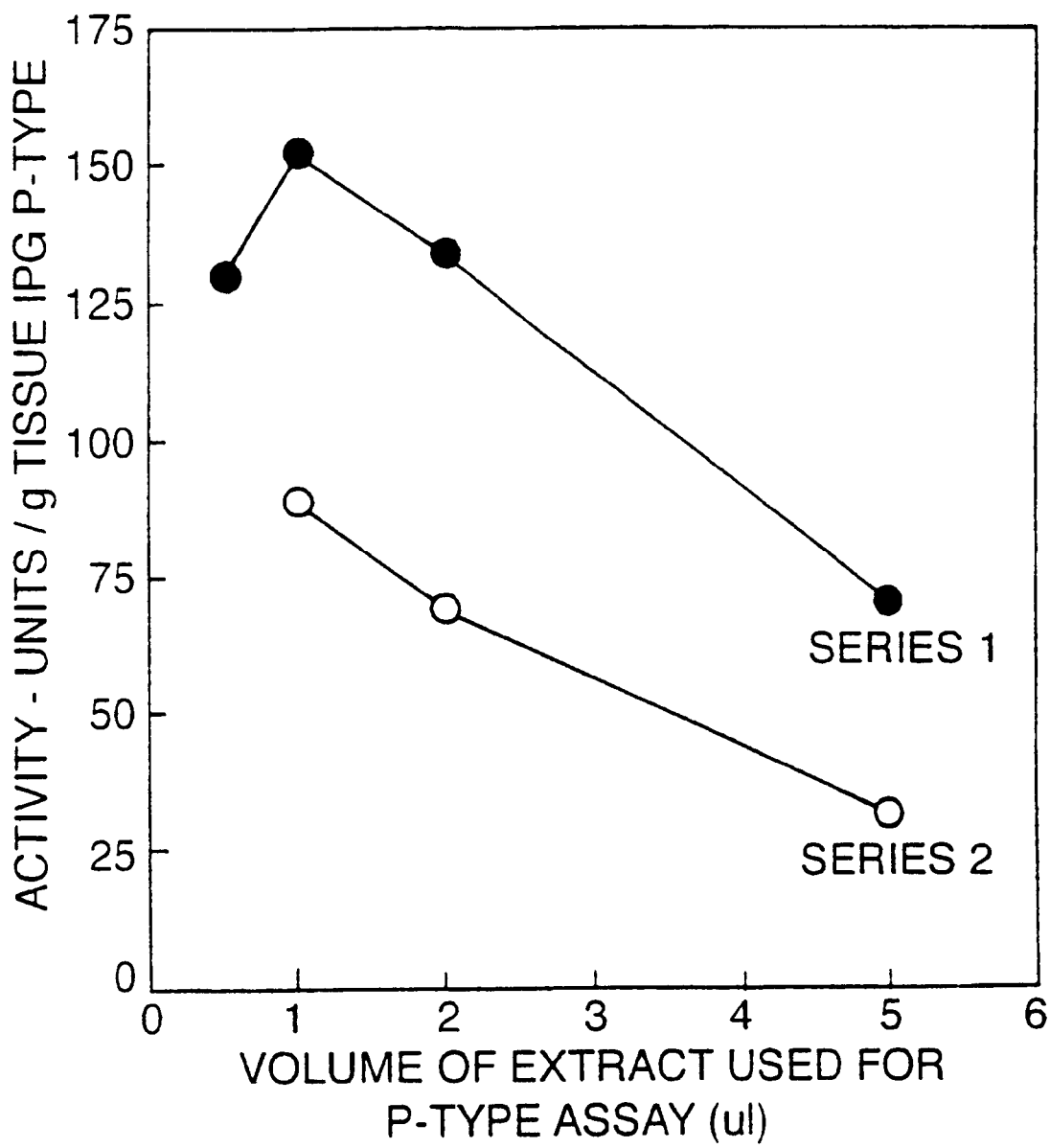

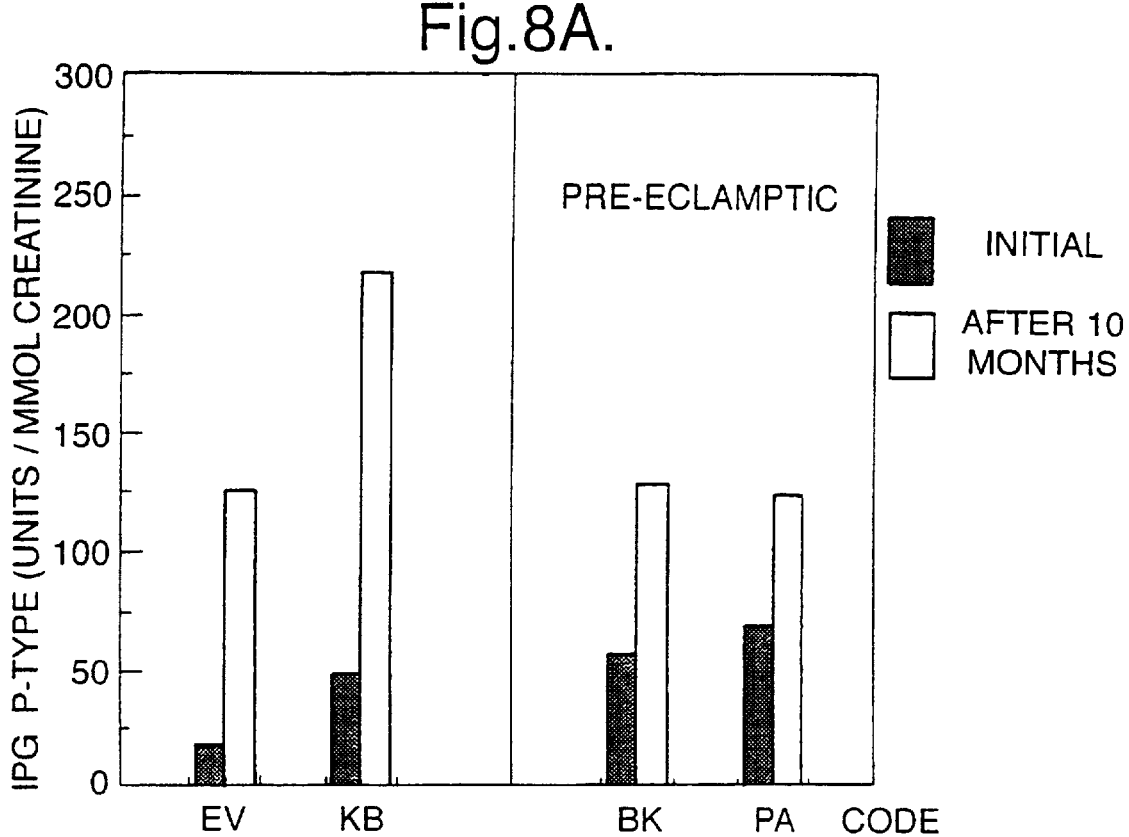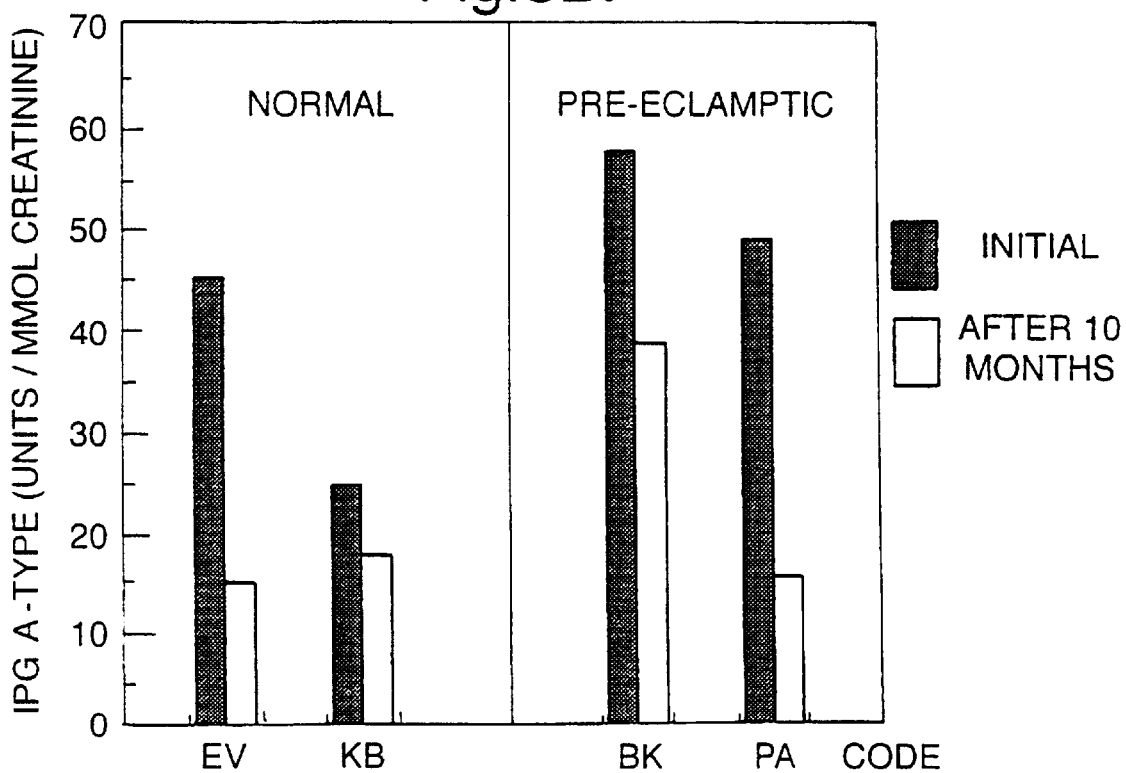

MATERIALS AND METHODS RELATING TO THE DIAGNOSIS AND TREATMENT OF PRE-ECLAMPSIA AND DIABETES

This Application is a 35 USC 371 of PCT/GB97/02523, filed Sep. 11, 1997.

1. Field of the Invention

The present invention relates to materials and methods for the diagnosis and treatment of pre-eclampsia and diabetes, and more particularly to the role of P-type inositolphosphoglycans (IPGs) in the occurrence of pre-eclampsia, methods of diagnosing pre-eclampsia and uses of antagonists of P-type IPGs in the treatment of pre-eclampsia.

2. Background of the Invention

Pre-eclampsia is a placental disease [1] characterised by insufficiency of the uteroplacental circulation [2], and which affects 10–12% of all pregnancies and is a major factor in the perinatal mortality rate. There is evidence that one or more placentally-derived factors are released into the maternal circulation which either directly or indirectly cause maternal endothelial dysfunction and ensuing maternal problems with activation of the clotting system increased vascular permeability and ischaemia in maternal organs secondary to vasoconstriction [3].

SUMMARY OF THE INVENTION

The present invention arises from investigations to determine whether there is a correlation between pre-eclampsia and its degree of severity and the profile of inositol phosphoglycans (IPGs) in the pre-eclamptic subjects and their normal age and parity-matched controls. In order to gain information on the significance of the disordered carbohydrate metabolism in the placenta in pre-eclampsia, as previously revealed by the massive increase in glycogen accumulation [4], comparison has been made with diabetic pregnant women in which placental glycogen accumulation is also a prominent feature [4,5], although not accompanied by the same degree of the life-threatening sequelae of pre-eclampsia.

Accordingly, in a first aspect, the present invention provides the use of a P-type inositolphosphoglycan (IPG) antagonist in the preparation of a medicament for the treatment of pre-eclampsia.

In further aspect, the present invention provides a method of treating pre-eclampsia in a patient, the method comprising administering a therapeutically effective amount of a P-type IPG antagonist to a patient.

In a further aspect, the present invention provides a pharmaceutical composition comprising a P-type antagonist in combination with a pharmaceutically acceptable carrier.

P-type IPGs and method for isolating them from human tissue are described below. This in turn allows those of ordinary skill in the art to prepare P-type IPG antagonists.

In the present invention, "P-type IPG antagonists" includes substances which have one or more of the following properties:

(a) inhibiting the release of P-type IPG from placenta;
(b) reducing the levels of placenta derived P-type IPG via an IPG binding substance (e.g. an antibody or a specific binding protein) against the placental derived TPG; and/or,
(c) reducing the effects of placenta derived P-type IPG.

In a further aspect, the present invention provides a method of screening for P-type IPG antagonists, the method comprising:

(a) contacting a candidate antagonist and a P-type IPG in an assay for a biological property of the P-type IPG under conditions in which the P-type IPG and the candidate antagonist can compete;
(b) measuring the biological property of the P-type IPG; and,
(c) selecting candidate antagonists which reduce the biological activity of the P-type IPG.

Some of the biological properties of P-type IPGs and assays to determine these properties that can be used in the above screening method are set out in the description below. The techniques of combinatorial chemistry are particularly suited to the production of large numbers of synthetic candidate antagonists, which can be screened for activity in the above method.

The particular emphasis placed upon the determination of the output of IPGs in both pre-eclamptic and diabetic pregnant women relates to the known fundamental importance of the class of compound in regulation key sites in metabolic pathways, resulting, in different tissues, in the direction of carbohydrates towards oxidation and glycogen synthesis in the case of the IPG P-type, or towards lipogenesis in the case of the IPG A-type; this regulation being both organ and inter-organ related [6, 9].

In copending applications claiming priority from GB-A-9618934.5, we report on the urinary content of IPGs in diabetic patients, from which evidence has been adduced for a critical role of altered inositol phosphoglycan profiles in relation to parameters linked to syndrome X, such as insulin resistance, obesity and high blood pressure. There are similarities between the metabolic changes in pre-eclampsia and syndrome X [10].

The results of our investigations described below indicate the following:

(a) The 24 hour output of IPG P-type in urine in pre-eclamptic women is significantly higher (2- to 3-fold) than in pregnant control subjects matched for age, parity and stage of gestation.
(b) Diabetic pregnant women do not show any significant change in urinary output of IPG P-type relative to pregnant control subjects matched for age, parity and gestational stage.
(c) Pregnancy itself is associated with an increased urinary output of IPG P-type relative to non-pregnant controls matched for age.
(d) No significant changes were found in the daily output of IPG A-type in pre-eclamptic or diabetic groups, with the exception of an increase in the IPG A-type in the pre-eclamptic group when the results were expressed as units per mmole creatinine.
(e) Urinary excretion of IPG P-type correlated with markers of the severity of pre-eclampsia, plasma alanine aspartate transaminase, degree of proteinuria and with platelet counts.
(f) Human placenta contained very high concentrations of IPG-P type, some 100×greater than either human or rat liver. It also appears to contain an inhibitor of IPG-P-ype activity as evidenced by a calculated decrease in activity when increasing the volume of the same preparation tested in the PDH phosphatase system (FIG. 7). Pre-eclamptic placenta contains approximately twice as much IPG-P type as does placenta from normal pregnant subjects. The IPG-A (pH 1.3 fraction) isolated from placenta showed no activity when tested for its ability to stimulate lipogenesis in rat adipocytes.
(g) Evidence has been found suggesting that the use of contraceptive pills may be related to an increase in IPG P-type in urine of normal women. (5 values only in each group).

(h) After storage for 10 months at −8° C., urine from pre-eclamptic women showed increased P-type activity (FIG. 8A) indicating that the urine initially contained a labile inhibitor. The yield of the IPG A-type isolated from the same urines decreased in activity (FIG. 8B).

(i) Significant differences were found between the ratios of IPG P-type and IPG A-type in non-pregnant women and normal male subjects; while the IPG P-type was similar in both groups, the IPG A-type was 5- to 6-fold higher in women.

(j) There is a 2.7 fold increase in IPG P-type in the urine of pre-eclamptic women, compared to normal pregnant subjects. There is a 2.7 fold increase in placenta-derived P-type mediators from pre-eclamptic women compared to normal pregnant subjects (See Table 5).

(k) The high urinary excretion IPG P-type in pre-eclampsia reflects high placental and circulating levels and is directly related to the accumulation of glycogen in the placenta in this condition, because IPG P-type activates glycogen synthase phosphatase.

(l) The concentration of P-type mediators in the urine of pre-eclamptic women returns baseline in post natal sample, (See FIG. 6) confirms that the source of the relevant P-type mediator in pre-eclamptic women is the placenta.

(m) A high circulating level of IPG P-type originating in the placenta may have paradrine effects, eg: in stimulating other endocrine glands, and/or affecting endothelial cells which could contribute to the pathogenesis of the pre-eclampsia syndrome.

The present invention provides, inter alia, a therapeutic treatment of pre-eclampsia:

(1) to inhibit the release of P-type mediator from placenta;
(2) to reduce the levels of placenta derived P-type IPG via antibody against the placental derived IPG;
(3) to reduce the effects of placenta derived P-type IPG via P-type antagonist.

The substance can be administered as the sole active substance, or as an adjunct to other forms of treatment. Because of their small molecular weight and heat and acid stability, IPGs should be suitable for oral administration, but other forms of administration are also contemplated. In the case of antibodies, or other proteins or substances which may not be suitable for oral administration, other methods such as parenteral administration may be used. Antibodies for administration are preferably human or "humanised" according to known techniques. This is discussed further below.

The invention also contemplates measurement of P-type IPG in blood or urine as a diagnostic for pre-eclampsia. Thus, in a further aspect, the present invention provides a method of diagnosing pre-eclampsia in a patient, the method comprising determining the level of P-type IPGs in a biological sample: obtained from the patient. Thus, a diagnosis can then be made by correlating this level with known levels of the P-type IPGS.

In one embodiment, the method comprises the steps of:
(a) contacting a biological sample obtained from the patient with a solid support having immobilised thereon binding agent having binding sites specific for one or more P-type IPGs;
(b) contacting the solid support with a labelled developing agent capable of binding to unoccupied binding sites, bound P-type IPGs or occupied binding sites; and,
(c) detecting the label of the developing agent specifically binding in step (b) to obtain a value representative of the level of the P-type IPGs in the sample.

As set out below, in this aspect of the invention, the level of the P-type IPGs can be further confirmed using a marker which correlates with the level of the P-type IPGs.

The present invention will now be described by way of example and not limitation with reference to the accompanying drawings.

BRIEF DESCRIPTION OF THE DRAWINGS

FIG. 6 shows a scheme setting out factors regulating placental glycogen metabolism in pre-eclampsia and diabetes.

FIG. 7 shows the effect of weight of tissue and volume used in assay on the estimation of P-type IPG in placenta of normal subjects.

FIGS. 8A, B show evidence for an unstable inhibitor of IPG-P type in the urine of pregnant women, both in normal and pre-eclamptic subjects, and the effect of storage of urine samples for 10 months at −80° C. on the P-and A-type IPG activity.

DETAILED DESCRIPTION OF THE INVENTION

IPGs

Figure 1:
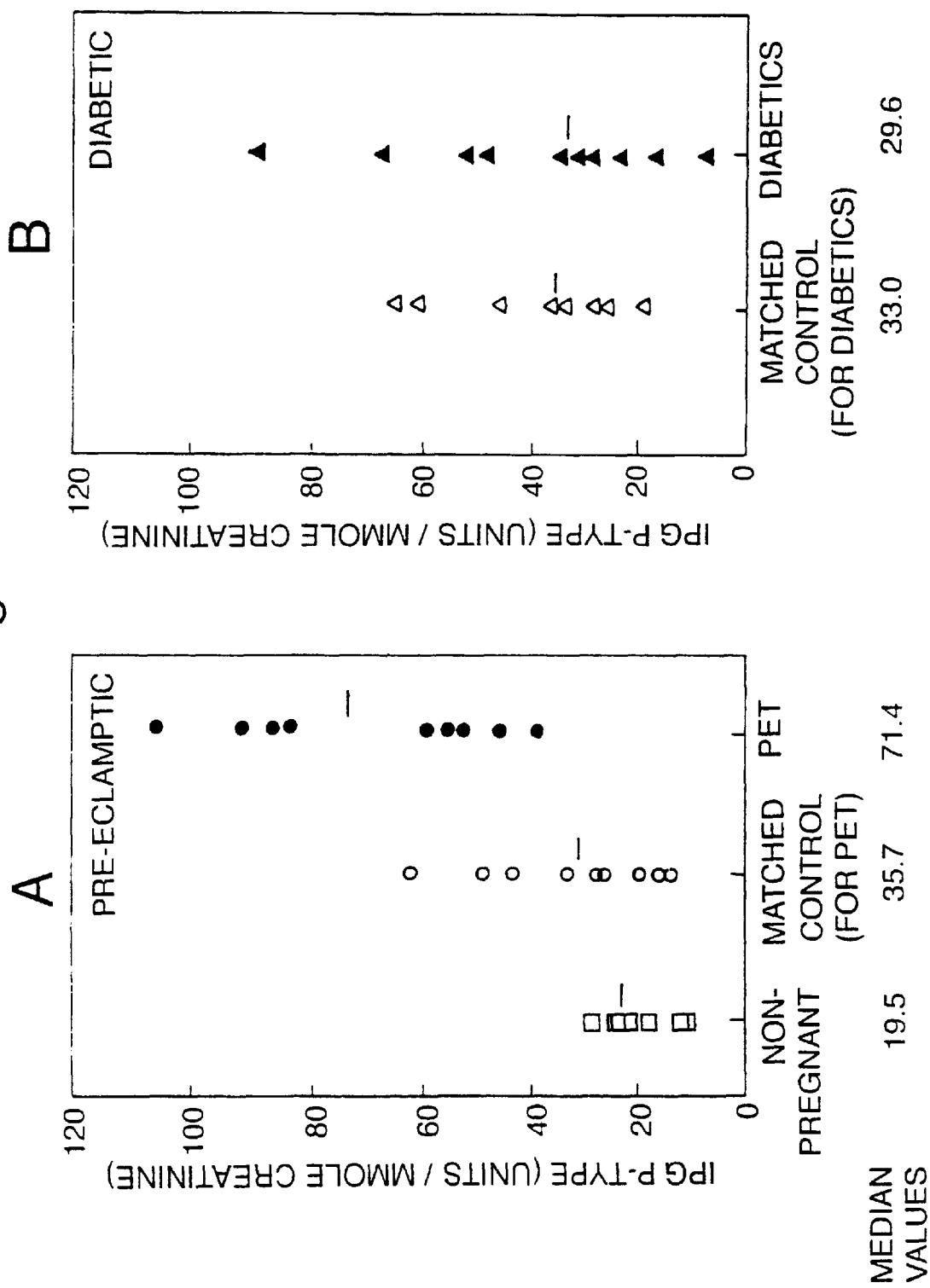
FIG. 1 shows (A, B) individual values for the concentration of IPG P-type (units/mmole creatine) in the urine of pregnant women in the pre-eclamptic group, diabetic group, in their respective matched normal pregnancy groups and in non-pregnant women, and (C, D) individual values for the concentration of IPG A-type (units/mmole creatine) in the urine of pregnant women in the pre-eclamptic group, diabetic group, and their respective matched normal pregnancy groups and non-pregnant women.
Figure 1:
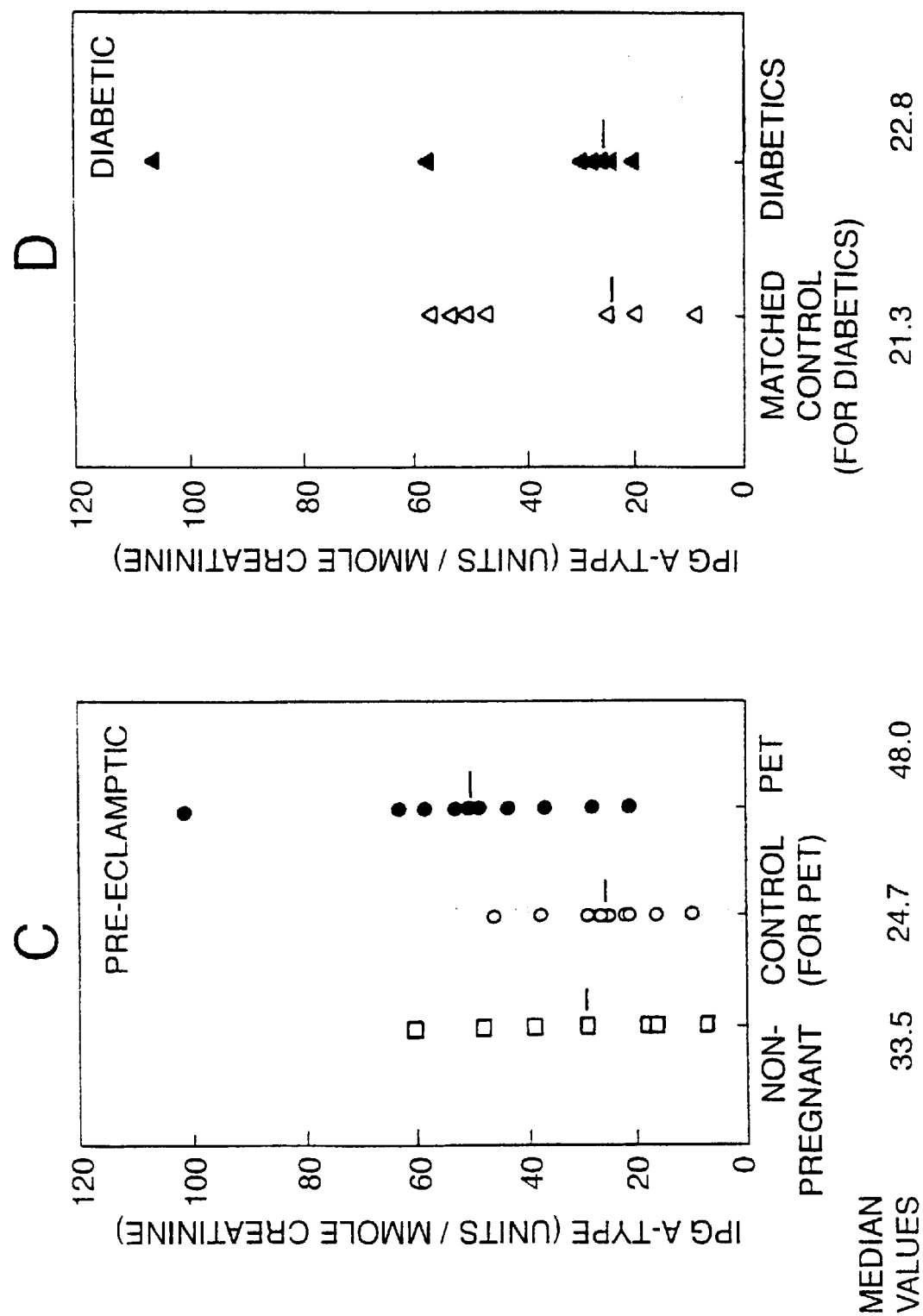

Studies have shown that A-type mediators modulate the activity of a number of insulin-dependent enzymes such as cAMP dependent protein kinase (inhibits), adenylate cyclase (inhibits) and cAMP phospho-diesterases (stimulates). In contrast, P-type mediators modulate the activity of insulin-dependent enzymes such as pyruvate dehydrogenase phosphatase (stimulates) and glycogen synthase phosphatase (stimulates). The A-type mediators mimic the lipogenic activity of insulin on adipocytes, whereas the P-type mediators mimic the glycogenic activity of insulin on muscle. Both A-and P-type mediators are mitogenic when added to fibroblasts in serum free media. The ability of the mediators to stimulate fibroblast proliferation is enhanced if the cells are transfected with the EGF-receptor. A-type mediators can stimulate cell proliferation in the chick cochleovestibular ganglia.

Soluble IPG fractions having A-type and P-type activity have been obtained from a variety of animal tissues including rat tissues (liver, kidney, muscle brain, adipose, heart, placenta) and bovine liver. A- and P-type IPG biological activity has also been detected in human liver and placenta, malaria parasitized RBC and mycobacteria. The ability of an anti-inositolglycan antibody to inhibit insulin action on human placental cytotrophoblasts and BC3H1 myocytes or bovine-derived IPG action on rat diaphragm and chick ganglia suggests cross-species conservation of many structural features. However, it is important to note that although the prior art includes reports of A- and P-type IPG activity in some biological fractions, the purification or characterisation of the agents responsible for the activity is not disclosed.

In our co-pending patent applications claiming priority from GB-A-9618930.3 and GB-A-9618929.5, we have described the isolation and characterisation of P-type and A-type IPGs.

A-type substances are cyclitol-containing carbohydrates, also containing $Zn^{2+}$ ion and optionally phosphate and having the properties of regulating lipogenic activity and inhibiting cAMP dependent protein kinase. They may also inhibit adenylate cyclase, be mitogenic when added to EGF-transfected fibroblasts in serum free medium, and stimulate lipogenesis in adipocytes.

P-type substances are cyclitol-containing carbohydrates, also containing $Mn^{2+}$ and/or $Zn^+$ ions and optionally phosphate and having the properties of regulating glycogen metabolism and activating pyruvate dehydrogenase phosphatase. They may also stimulate the activity of glycogen synthase phosphatase, be mitogenic when added to fibroblasts in serum free medium, and stimulate pyruvate dehydrogenase phosphatase.

The A- and P-type substances were also found to have the following properties:

1. Migrates near the origin in descending paper chromatography using 4/1/1 butanol/ethanol/water as a solvent.
2. The substances contains phosphate which is directly related to activity.
3. The free GPI precursors are resistant to cleavage by GPI-PLC.
4. They are bound on Dowex AG50 (H+) cation exchange resin.
5. They are bound on an AG3A anion exchange resin.
6. The activity is resistant to pronase.
7. They are detected using a Diones chromatography system.
8. The P-type substance is partially retained on C-18 affinity resin.

The A- and P-type substances may be obtained from human liver or placenta by:

(a) making an extract by heat and acid treatment of a liver homogenate, the homogenate being processed from tissue immediately frozen in liquid nitrogen;
(b) after centrifugation and charcoal treatment, allowing the resulting solution to interact overnight with an AG1-X8 (formate form) anion exchange resin;
(c) collecting a fraction having A-type IPG activity obtained by eluting the column with 50 mM HCl, or a fraction having P-type IPG activity obtained by eluting the column with 10 mM HCl;
(d) neutralising to pH 4 (not to exceed pH 7.8) and lyophilising the fraction to isolate the substance.
(e) descending paper chromatography using 4/1/1 butanol/ethanol/water as solvent.
(f) purification using high-voltage paper electrophoresis in pyridine/acetic acid/water.
(g) purification using Dionex anion exchange chromatography or purification and isolation using Vydac 301 PLX575 HPLC chromatography.

More details of the methods for obtaining these IPGs are provided in the said patent applications, the contents of which are incorporated herein by reference.

Antagonists

As mentioned above, antagonists of P-type activity, either naturally occurring or synthetic, inlcude substances which have one or more of the following properties:

(a) substances capable of inhibiting release of P-type mediator from placenta;
(b) substances capable of reducing the levels of placenta derived P-type IPG via an IPG binding substance (e.g. an antibody or specific binding protein) against the placental derived IPG; and/or,
(c) substances capable of reducing the effects of placenta derived P-type IPG.

In one embodiment, the IPG antagonists are specific binding proteins. Naturally occurring specific binding proteins can be obtained by screening biological samples for proteins that bind to IPGs.

In a further embodiment, the antagonists are antibodies. The production of polyclonal and monoclonal antibodies is well established in the art, and exemplary protocols are set out in the examples below. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-239400. A hybridoma producing a monoclonal antibody may be subject to genetic mutation or other changes, which may or may not alter the binding specificity of antibodies produced.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357:80–82, 1992). Isolation of antibodies and/or antibody-producing cells from an animal may be accompanied by a step of sacrificing the animal.

As an alternative or supplement to immunising a mammal with a peptide an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments) , or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab') 2 fragments, a bivalent fragment including two Fab fragments linked by a disulphide bridge at the hinge region. Single chain Fv fragments are also included.

Humanised antibodies in which CDRs from a non-human source are grafted onto human framework regions, typically with the alteration of some of the framework amino acid residues, to provide antibodies which are less immunogenic than the parent non-human antibodies, are also included within the present invention.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The antibodies described above may also be employed in the diagnostic aspects of the invention by tagging them with a label or reporter molecule which can directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenizidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

In a further embodiment, the IPG antagonists are synthetic compounds. These may be produced by conventional chemical techniques or using combinatorial chemistry, and then screened for IPG antagonist activity. These compounds may be useful in themselves or may be used in the design of mimetics, providing candidate lead compounds for development as pharmaceuticals. Synthetic compounds might be desirable where they are comparatively easy to synthesize or where they have properties that make them suitable for administration as pharmaceuticals, e.g. anatgonist which are peptides may be unsuitable active agents for oral compositions if they are degraded by proteases in the alimentary canal. Mimetic design, synthesis and testing is generally used to avoid randomly screening large number of molecules for a target property.

Production of Monoclonal Antibodies

Inositolphosphoglycan (IPG) purified from rat liver by sequential thin layer chromatography (TLC) was used to immunize New Zealand rabbits and Balb/c mice by using conventional procedures.

After immunisation, monoclonal antibodies were prepared using the approach of fusion of mouse splenocytes ($5 \times 10^6$ cells/ml) with mutant myeloma cells ($10^6$ cells/ml). The myeloma cell lines used were those lacking hypoxanthine-guanine phosphoribasyl transferase. The screening method of hybridoma cells was based on a non-competitive solid-phase enzyme immunoassay in which the antigen (IPG) was immobilised on a solid phase. Culture supernatant were added and positive hybridoma cells were selected.

A single cell cloning was made by limiting dilution. Hybridomas for three monoclonal antibodies (2D1, 5HG and 2P7) were selected. All monoclonal antibodies were determined to be IgM using a EK-5050 kit (Hyclone).

In order to test that all monoclonal antibodies recognised IPGs, a non-competitive solid-phase enzyme immunoassay was used. F96 Polysorp Nunc-Immuno Plates are used for the assay. The polysorp surface is recommended for assays where certain antigens are immobilised.

The immobilised antigen (IPG) diluted to 1:800 captured the monoclonal antibody from tissue culture supernatant, ascitic fluid, and when the purified monoclonal antibody was used.

The detection method used an anti-mouse IgM, biotinylated whole antibody (from goat) and a streptavidin-biotinylated horseradish peroxidase complex (Amersham), ABTS and buffer for ABTS (Boehringer Mannheim).

The same immunoassay was used to evaluate the polyclonal antibody. In this assay, the detection method employed an anti-rabbit Ig, biotinylated species—specific whole antibody (from donkey).

The antibodies can be purified using the following method. Fast Protein Liquid Chromatography (Pharmacia FPLC system) with a gradient programmer GP-250 Plus and high precision pump P-500 was used in order to purify a polyclonal IPG antibody.

A HiTrap protein A affinity column was used for purification of polyclonal IPG from rabbit serum, Protein quantitation was made using a Micro BCA protein assay reagent kit (Pierce).

Monoclonal IgM antibodies were purified in two steps. Ammonium sulfate precipitation was the method chosen as a first step. Tissue culture supernatant was treated with ammonium sulfate (50% saturation). Pellet diluted in PBS was transferred to dialysis tubing before the second step.

Since ammonium sulfate precipitation is not suitable for a single step purification, it was followed by gel filtration chromatography-antibody solution in PBS run into a Pharmacia Sepharose 4B column. Protein quantitation was made reading the absorbance at 220–280 nm in a Perkin-Elmer lambda 2 UV/VIS spectrophotometer.

Protocol for Sandwich ELISA

The protocol below sets out an indirect, non-competitive, solid-phase enzyme immunoassay (sandwich ELISA) for the quantification of inositolphosphoglycans (IPG) in biological fluids, such as human serum.

In the assay, monoclonal IgM antibodies are immobilised on a solid phase. Tissue culture supernatant, ascitic fluid from mice with a peritoneal tumour induced by injecting hybridoma cells into the peritoneum and purified monoclonal antibody have been used in the immunoassay. F96 Maxisorp Nunc-Immuno plates were used for these assays. Maxisorp surface is recommended where proteins, specially glycoproteins such as antibodies, are bound to the plastic.

The immobilised antibody captures the antigen from the test sample (human serum or IPG used like a positive control).

A bridging antibody (a purified polyclonal IPG antibody from rabbit) is needed to link the anti-antibody biotinylated to the antigen.

The detection method employs an anti-rabbit Ig, biotinylated species-specific whole antibody (from donkey) and a sureptavidin-biotinylated horseradish peroxidase complex (Amersham), ABTS and buffer for ABTS (Boehringer Mannheim).

The ELISA assay can be carried out as follows:

1. Add 100 $\mu$l/well in all the steps.
2. Add monoclonal antibody diluted 1:100 in PBS in a F96 Maxisorp Nunc-Immuno plate. Incubate at least 2 days at 4° C.
3. Wash with PBS three times.
4. Add a blocking reagent for ELISA (Boehringer Mannheim) in distilled water (1:9) 2 hours at room temperature.
5. Wash with PBS-Tween 20 (0, 1%) three times.
6. Add a purified polyclonal antibody (diluted 1:100 in PBS), overnight at 4° C.
7. Wash with PBS-Tween 20 (0.1%) three times.
8. Add an anti-rabbit Ig, biotinylated species-specific whole antibody (from donkey) (Amersham) diluted 1:1000 in PBS, 1 h 30 min at room temperature.
9. Wash with PBS-Tween 20 (0.1%) three times.
10. Add a streptavidin-biotinylated horseradish peroxidase complex (Amersham) diluted 1:500 in PBS, 1 h 30 min at room temperature.
11. Wash with PBS three times.
12. Add 2.2-Azino-di-(3-ethylbenzthiazoline sulfonate (6)) diammonium salt crystals (ABTS) (Boehringer Mannheim) to buffer for ABTS (BM) : Buffer for ABTS is added to distilled water (1:9 v/v). 1 mg of ABTS is added to 1 ml of diluted buffer for ABTS.
13. Read the absorbance in a Multiscan Plus P 2.01 using a 405 mm filter in 5–15 min.

Pharmaceutical Compositions

The antagonists of the invention can be formulated in pharmaceutical compositions. These compositions may comprise, in addition to one or more of the P-type antagonists, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, antibody, peptide, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition may be administered alone or in combination with other treatments, either simultaneously or sequentially dependent upon the condition to be treated.

Diagnostic Methods

Methods for determining the concentration of analytes in biological samples from individuals are well known in the art and can be employed in the context of the present invention to determine whether an individual has an elevated level of P-type IPGs, and so has or is at risk from pre-eclampsia. The purpose of such analysis may be used for diagnosis or prognosis to assist a physician in determining the severity or likely course of the pre-eclampsia and/or to optimise treatment of it. Examples of diagnostic methods are described in the experimental section below.

Preferred diagnostic methods rely on the detection of P-type IPGs, an elevated level of which was found to be associated with pre-eclampsia. The methods can employ biological samples such as blood, serum, tissue samples (especially placenta), or urine.

The assay methods for determining the concentration of P-type IPGs typically employ a binding agent having binding sites capable of specifically binding to one or more of the P-type IPGs in preference to other molecules. Examples of binding agents include antibodies, receptors and other molecules capable of specifically binding P-type IPGs. Conveniently, the binding agent is immobilised on solid support, e.g. at a defined location, to make it easy to manipulate during the assay.

The sample is generally contacted with a binding agent under appropriate conditions so that P-type IPGs present in the sample can bind to the binding agent. The fractional occupancy of the binding sites of the binding agent can then be determined using a developing agent or agents. Typically, the developing agents are labelled (e.g. with radioactive, fluorescent or enzyme labels) so that they can be detected using techniques well known in the art. Thus, radioactive labels can be detected using a scintillation counter or other radiation counting device, fluorescent labels using a laser and confocal microscope, and enzyme labels by the action of an enzyme label on a substrate, typically to produce a colour change. The developing agent can be used in a competitive method in which the developing agent competes with the analyte (P-type IPG) for occupied binding sites of the binding agent, or non-competitive method, in which the labelled developing agent binds analyte bound by the binding agent or to occupied binding sites. Both methods provide an indication of the number of the binding sites occupied by the analyte, and hence the concentration of the analyte in the sample, e.g. by comparison with standards obtained using samples containing known concentrations of the analyte.

EXPERIMENTAL DESCRIPTION

A. Experimental

1. Assay of IPG A-type and IPG P-type Activity

The activity of P- and A-type IPGs in urine and placental extracts were studied using specific bioassay procedures. IPG P-type was determined using the activation of PDH phosphatase [11]. The PDH complex and PDH phosphatase (metal-dependent form) were prepared from beef heart as described by Lilley et al. [11] and the assay of the activation of the phosphatase was performed by the spectrophotometric variant of the two-stage system described by these authors. This assay is considered to be a characteristic feature of IPG P-type (see Larner et al. [12]) . IPG A-type was determined by the stimulation of lipogenesis as measured by the incorporation of $[U^{14}C]$ glucose into the lipids of adipocytes isolated from epididymal fat pads by the method of Rodbell [13]. A high degree of specificity for IPG A-type was found for this bioassay.

A straight line relationship between added IPGs and the stimulation of PDH phosphatase activity (IPG P-type) and lipogenesis in intact adipocytes (IPG A-type) was obtained; this relationship held at least up to a stimulation of +250%. These observations provided a basis for a unit to be defined and used for the purpose of comparison of yields of IPGs from different tissues and urine samples. Linearity between IPG added and the percentage change in response, has been observed by others (see Lilley et al. [11] and Newman et al. [14]), although Asplin et al. [15] did not show linearity in their study on IPGs in human urine from normal and diabetic subjects, an effect which was particularly marked with the IPG A-type (pH 1.3 fraction).

2. Extraction of IPG P-type and IPG A-type from Urine

Urines were extracted as described by Asplin et. al. [15]. The final fractions were freeze dried and stored at $-20°$ C. For use, the IPG fractions were resuspended in water, immediately before assay, so that 10 $\mu$l of redissolved IPG corresponded to 10 ml urine.

In view of the possibility that high, and varying, amounts of IPGs might be excreted in the different groups of pregnant and pre-eclamptic subjects, and in order to ensure that the capacity of the resin was well in excess of the load applied, preliminary test runs were made to determine the optimal ratio of resin to starting urine volume. Linearity of recovery was obtained up to 100 ml urine per 18 g resin. In the present study, the ratio of 30 ml urine to 18 g resin was maintained to allow for variation in IPG content.

3. Preparation of Placenta

In preliminary studies two normal placentae were obtained and treated as follows:

(i) The first was collected within 40 minutes of delivery and samples of the tissue were freeze-clamped and stored and transported in solid $CO_2$.

(ii) The second placenta was collected an estimated 30 minutes post-delivery and a 15 g sample freeze-clamped immediately. The remainder was divided into two, one half stood at room temperature and the other stored in ice. 10 g samples from each of these halves were removed after 1, 3 and 5 hours, freeze-clamped and treated as above.

These samples were stored at $-80°$ C. until extracted.

4. Extraction of Inositol Phosphoalvcans from Placenta

The extraction procedure involved pulverising the frozen tissue (5 g) under liquid nitrogen and then extracting with 50 mM formic acid at $100°$ C. for 3 minutes. The supernatant fraction, after centrifugation, was treated with charcoal (10 mg/ml) and again centrifuged. The charcoal supernatant was passed through a Millipore filter, diluted 5-fold with water and then brought to pH 6 with ammonia. After centrifugation, the extract was added to 15 g AG1-X8 and stood overnight at $0°$ C. The resin was then transferred to columns and washed with 40 ml water followed by 40 ml of HCl, pH3. IPG P-type was eluted with 100 ml of HCl, pH 2.0, and IPG A-type with 100 ml HCl, pH 1.3. The extracts were brought to pH 4 with ammonia and rotary evaporated to about 5 ml before being transferred to smaller tubes and freeze dried. It was stored in this state at $-20°$ C. until used. This extraction procedure was based on that described by Nestler et. al. [16].

The wide variations in inositol phosphoglycan content of different tissues [91 prompted the preliminary examination of:

(i) the optimal weight of placental tissue relative to the weight of resin to be used in the isolation and separation of IPG P-type and IPG A-type and (ii) the amount of the isolated fractions to be used in the bioassay systems to ensure that the assays fell within the linear portion of dose-response curve.

Figure 10:
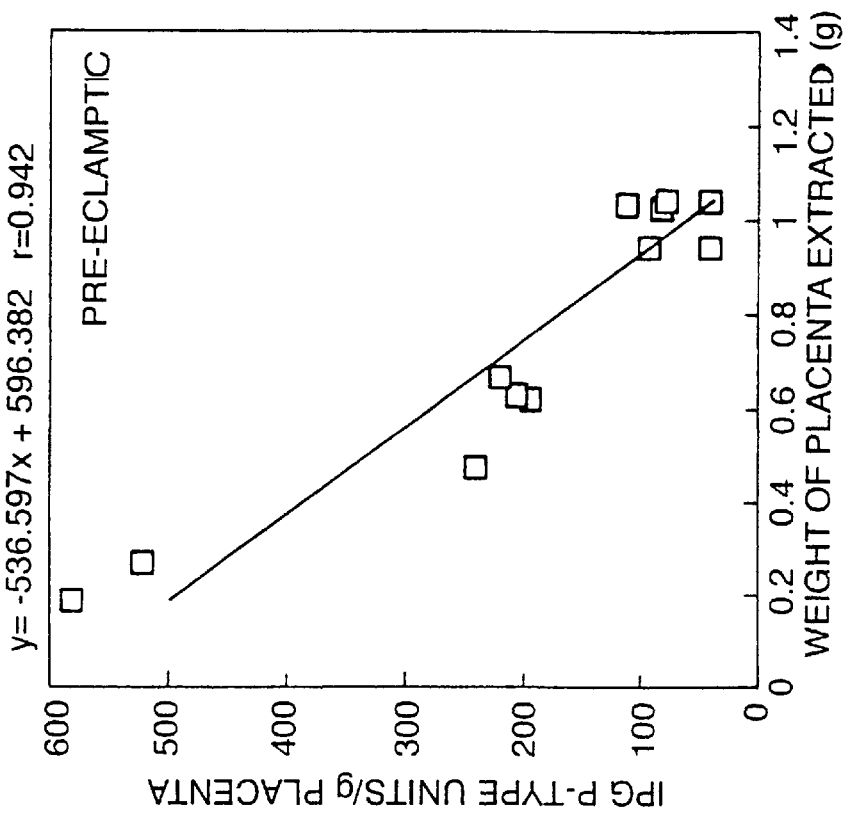
FIGS. 9 and 10 shows the relationship between the yield of P-type IPG and the weight of placental tissue extracted in normal and pre-eclamptic subjects.
Figure 9:
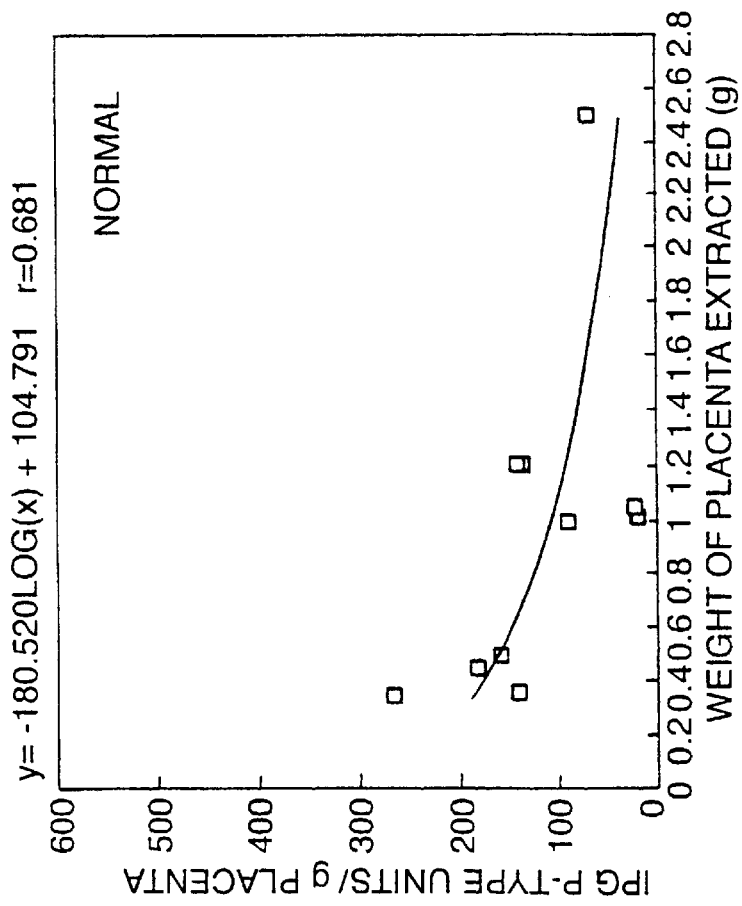

It was established that, using a column containing 18 ml resin, maximum IPG-P type activity was recovered when placenta samples were less than 0.3 g (FIGS. 9 and 10) and that the final assay was most reliable when the IPG P-type so obtained was resuspended in 100 $\mu$l water, of which 1 or 2 $\mu$l were used for assay in the PDH phosphatase activation system. Under these conditions, a stimulation of up to +300% was obtained and the response was linear within the parameters given. When amounts of placenta greater than 0.3 g were used, the yield of P-type IPG (calculated per gram extracted) fell sharply, either due to the co-extraction of a potent inhibitor or the presence of materials competing for the available binding sites on the resin.

No activity of IPG A-type, as evidenced by stimulation of lipogenesis in rat adipocytes, was detected. Six separate pH 1.3 extracts prepared from placenta; 4 separate extractions were tested, all in triplicate. Parallel extractions of rat liver, carried out at the same time, yielded values of 1.92 units/g and an insulin standard assayed at the same time gave a stimulation above base-line of +258%.

5. Expression of Results

A unit of IPG is defined as the amount causing a 50% activation in the basal level of the test system.

The yield of IPGS in urine is given on three different bases:

(i) Percentage stimulation of the test system by 10 μl final urine extract (Col 1), allowing direct comparison with data of Asplin et. al. [15]

(ii) Units of IPG per 1 mmol creatinine.

(iii) Units of IPC found in a sample of a 24 hour collection or urine; ie: the total daily output at that stage of gestation.

The results are given as means ± SEM and are evaluated either on the basis of the corresponding paired sample, the selection of subjects being matched for stage of gestations, parity and age, or on the basis of the Mann-Whitney ranking test for non-parametric data.

6. Design of Experiment

The ten pre-eclamptic and pregnant diabetic women studied were each matched with a normal pregnancy control subject for stage of gestation (±13 days), parity (0, 1–3, 4+) and age (±4 years). The gestational range was from 26 to 37 weeks for the pre-eclamptic group and from 31 to 38 weeks for the diabetic pregnant group. Normal non-pregnant women of reproductive age were included to allow evaluation of the effect of pregnancy per se on urinary excretion of inositol phosphoglycans.

The changes in inositol phosphoglycans in pre-eclampsia were correlated with the severity of the condition.

Urine: Creatinine, urea. $Na^+$, $K^+$, $Ca^+$ protein and volume / 24 hours.

Blood: Creatinine, aspartate transaminase (liver enzyme marker), platelet counts.

Biodata: Age, gestational age, parity, blood pressure, birth weight, placental weight.

B. Results

1. Stability of Inositol Phoshoglycans Isolated from the Placenta:

Material from the first placenta, freeze-clamped immediately on receipt from the delivery room, gave exceptionally high yields of IPG P-type, no activity of IPG A-type was found.

The activity of the immediate sample from the second placenta was appreciably less but, nevertheless, contained approximately 7 units of activity/g. Samples from this placenta stored at room temperature 1, 3 or 5 hours were all devoid of IPG P-type activity. The sample stored on ice for 1 hour had lost approximately half of its activity compared to the immediate freeze-clamped sample, while those stored for 3 or 5 hours both yielded less than 1 unit of activity/g. It is concluded that IPGs are highly unstable in untreated tissue, even at 0° C.

2. Inositol Phosphoglycans in Placenta Delivered at Term:

The values for units/g tissue of extracted IPG P-type and IPG A-type are show in Table 1 for the human placenta, human liver and rat liver. The exceptionally high value for the IPG P-type in placenta is apparent.

The occurrence of a very high IPG P-type in placenta is in accord with the known function of this putative insulin mediator on steroidogenesis in this tissue, and with the reported action of IPG P-type in activating glycogen synthase phosphatase [16, 17]. Further, as a first approximation, it may be held that an increase in urinary IPG P-type in pregnancy, whether in normal pregnant, diabetic or pre-eclamptic subjects, originates in the placenta. Thus, measurements of the concentration and 24-hour daily excretion of IPG P-type may be an indicator of placental production of this mediator.

A comparative study of pre-eclamptic and normal placental tissue demonstrates a 2.7 fold increase in IPG P-type in the pre-eclamptic placenta (See Table 5).

The inability of the pH 1.3 fractions from all six placenta studied to stimulate lipogenesis in rat adipocytes may indicate a high degree of tissue specificity for the placental IPG A-type and a very specialized function for placental IPG A-type.

3. Inositol Phosphoglycans in Urine in Pre-eclampsia and Diabetes:

The concentration and total daily output of inositol phosphoglycans in the urine of pre-eclamptic or pregnant diabetic and control subjects are given in Table 2. The results are given as the stimulation of the bioassay system produced by 10 μl of the IPG P-type (pH 2.0) or the IPG A-type (pH 1.3) fractions to allow comparison with the data of Asplin et. al. [15]. The results are also shown as units/mmol creatinine and as the 24-hour daily output in units. The most striking difference was seen in the IPG P-type in the pre-eclamptic group which was two to three-fold higher than the matched control group. Diabetes did not result in a significant difference in the inositol phosphoglycans in urine relative to their control group at the same stage of pregnancy. The individual values showing the range of values for pre-eclamptic, diabetic and control groups are presented in FIGS. 1 A, B.

An interesting difference resides in the present observation that the non-pregnant control group had a lower IPG P-type concentration and total daily excretion than the pregnant control groups for the pre-eclamptic and diabetic subjects (see Table 2). These differences were statistically significant.

The striking finding that the pre-eclamptic group alone showed a significant increase of P-type amongst the pregnant women, and that the IPG P-type was lower in the non-pregnant group, provided evidence for a link between pre-eclampsia and the production of this inositol phosphoglycan.

That the increased urinary IPG P-type originates in the placenta is strongly suggested by the present observation that all pregnant subjects had a raised IPG P-type value relative to the non-pregnant controls and that the placenta itself has an outstandingly high endogenous concentration of IPG P-type (see Table 5).

If the higher excretion rate of IPG P-type in pre-eclamptic subject and their matched controls compared to normal non-pregnant subjects is equated to the contribution of the placenta to urinary IPG P-type (Table 2), then the effect of pre-eclampsia is even more starkly underlined with the pre-eclamptic values being some 5- to 6- times greater than the pre-eclamptic control "control for the pre-eclamptic group" values for all modes of expression (Table 3) . This interpretation is strengthened when a similar calculation is made for the IPG A-type. In this case, there is no 'excess' IPG A-type that can be ascribed to the presence of the placenta, a finding in accord with the present inability to demonstrate the presence of the A-type in this tissue (see Table 1) Also, values fall post-natally, as shown in FIG. 6.

The only significant difference in urinary IPG A-type recorded in Table 2 and FIG. 1 C, D was the raised value in pre-eclamptic subjects when the results were expressed as units/mmole creatinine. No difference was seen in the 24 hour output of IPG A-type in this condition.

Figure 2:
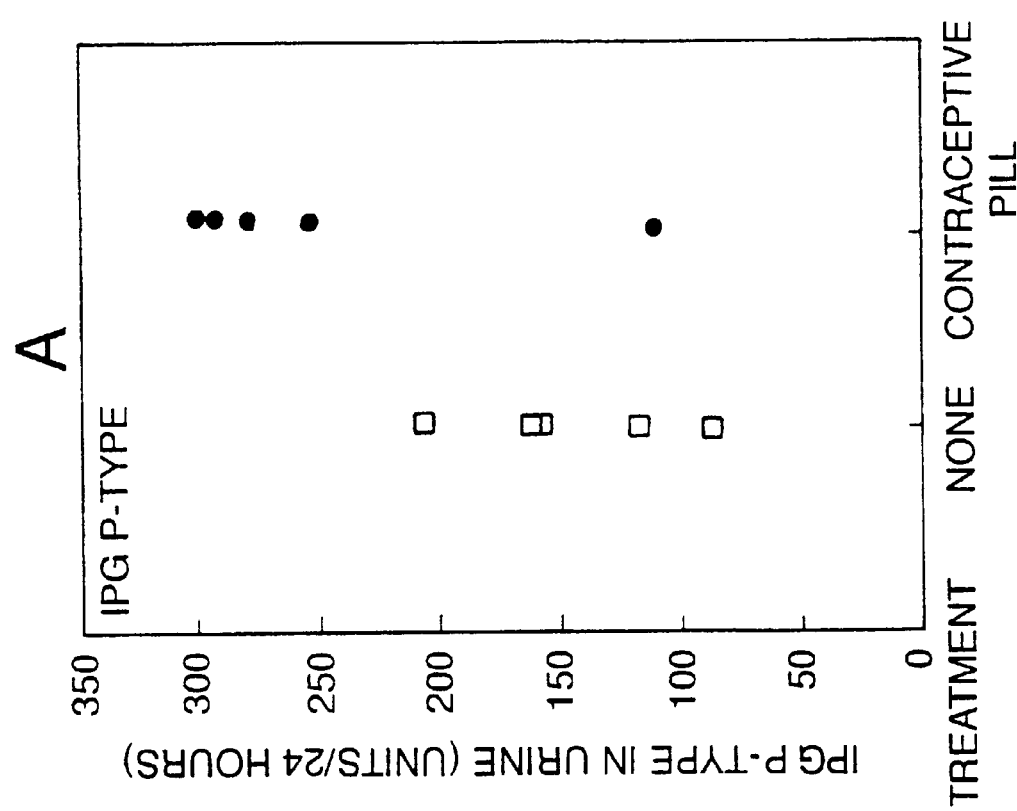
FIGS. 2A, B shows the effect of the contraceptive pill on urinary output of IPG P-type and IPG A-type in non-pregnant control subjects.

4. Inositol Phosphoglycans in Non-pregnant Subjects:

The ten non-pregnant subjects in this study included five on the contraceptive pill and in order to determine if the altered hormone background might influence the profile of inositol phosphoglycans, these two sub-sets were considered separately. These data are shown in FIG. 2 from which it can be seen that there is some evidence for a higher output of P-type in the group taking contraceptive pills. The number of subjects in each sub-set is too small on which to base firm conclusions but, nevertheless, the results suggest that an extension of this survey is merited.

In a separate project, on the changes in urinary IPGs in male diabetic subjects attending the out-patients clinic at The Middlesex Hospital, a group of normal males was involved. Comparison of the data from that study with those from the present study of normal non-pregnant females revealed the interesting finding that while the IPG P-type/mmol creatinine was similar in both groups, the IPG A-type was significantly higher in the normal female urine samples by 5- to 6-fold (Table 4). There was a marked difference in the IPG P-/IPG A- ratio, which was 0.6 for women and 3.1 for men.

5. Inositol Phosphoglycans and Stage of Gestation:

In view of the evidence for a progressive decrease in the activity of a number of placental enzymes involved in glucose metabolism and in placental glycogen content towards the end of gestation [5, 18–20], the present data on urinary inositol phosphoglycans were examined with respect to the stage of gestation at which the samples were taken; this varied between 26–37 weeks.

While these data must be interpreted with caution in view of the small number of samples at the earlier stages of gestation and the possible weighting by one remarkably high value at 26 weeks, certain trends are apparent.

Figure 3:
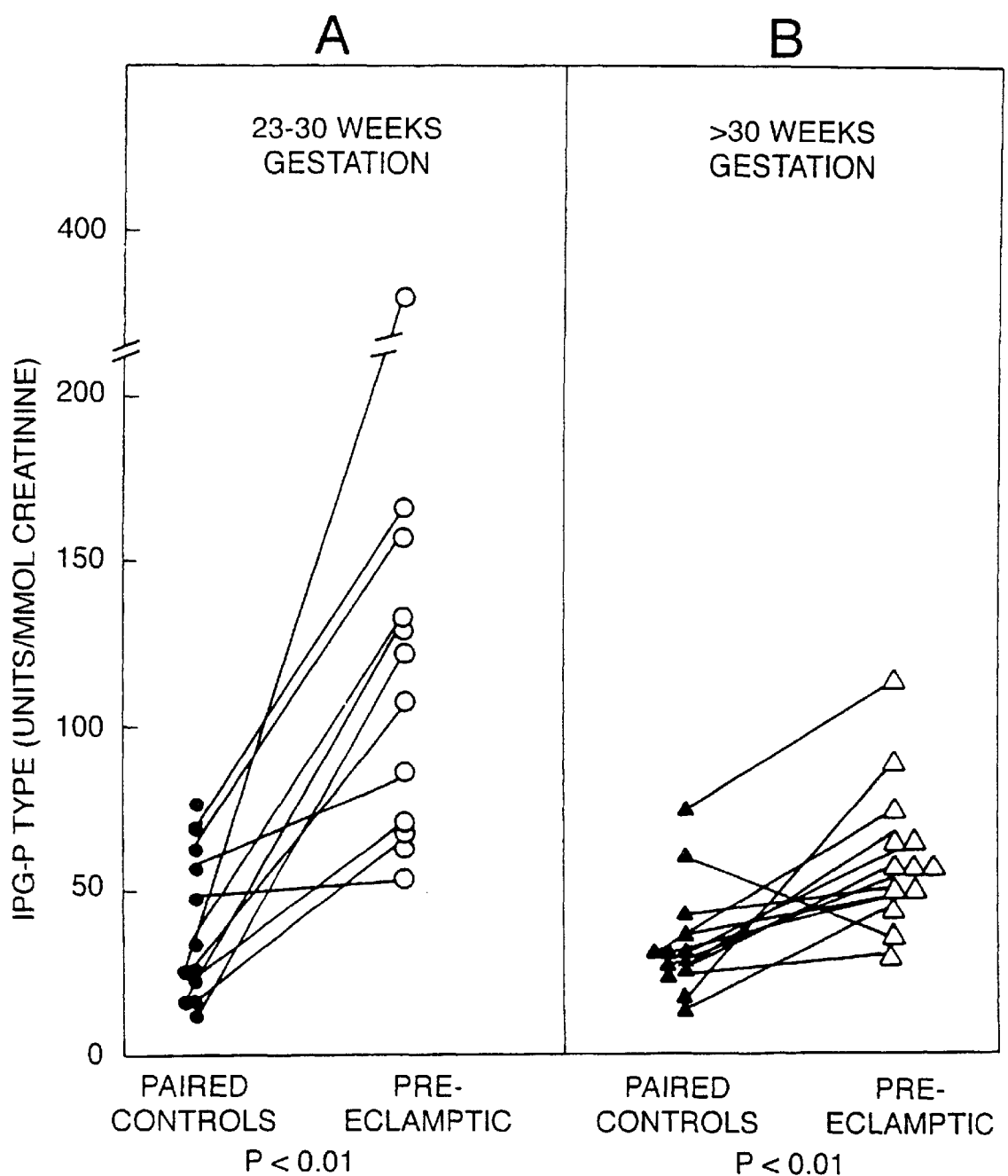
FIGS. 3A, B shows the relationship between P-type and stage of gestation at which samples were collected from groups of pre-eclamptic, diabetic and matched control pregnant women.

There was a significant correlation between the stage of gestation and IPG P-type in the urine of pre-eclamptic subjects (r=0.609; P<0.05) (FIG. 3A), the highest values of IPG P-type being found at the beginning of the third trimester, the values for pre-eclamptic and age-matched control groups approximating closely in the period 35–37 weeks. No such correlation was seen with the diabetic or normal control groups (see FIG. 3B). Further, no correlation was found between IPG A-type in urine and the stage of gestation.

In this present study, single 24 hour urine collections were made at different stages in the period 26–37 weeks of pregnancy. It is open to speculation whether the differences between IPG P-type in the urine of the pre-eclamptic group and their matched controls reflect a relative immaturity of the cells in the pre-eclamptic subjects [4, 21], and a delay in a naturally occurring decline in IPG P-type production towards the end of gestation, or whether the significant raised values of IPG P-type in the pre-eclamptic group is a specific marker for the degree of severity of pre-eclampsia. The question of the possible changes in IPG P-type in urine at different stages of pregnancy remains to be answered by measurements of urinary IPGs in the same subject at timed intervals throughout pregnancy.

6. Urinary Inositol Phosphoglycans and Markers for Pre-eclampsia:

6.1 IPG P-type and Markers of Pre-eclampsia:

The IPG P-type excreted was examined in relation to markers of pre-eclampsia, including protein in urine, the activity of alanine-aspartate transaminase in plasma and blood pressure, all known to increase in pre-eclampsia, and platelet counts which decrease.

Figure 4:
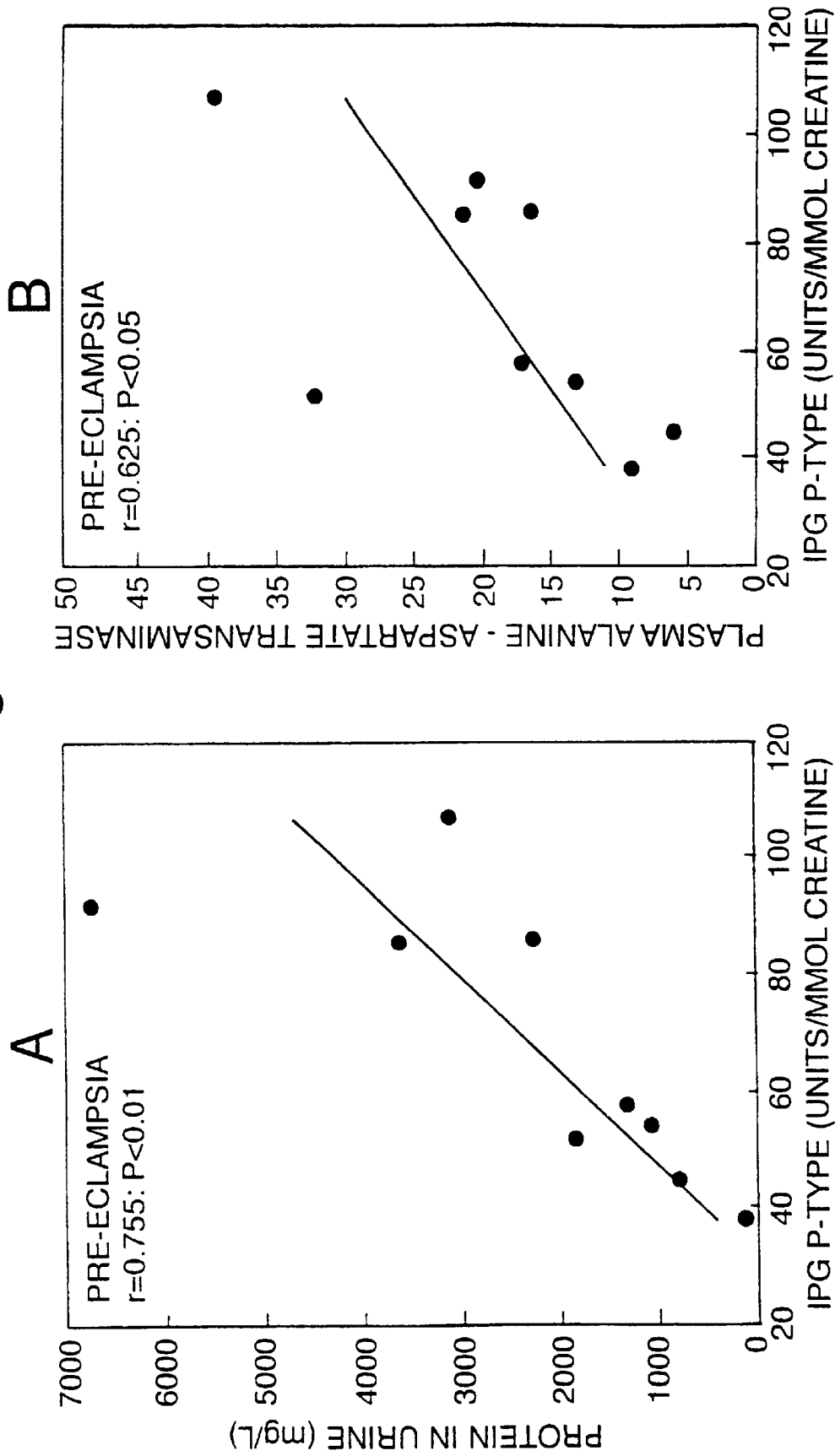
FIG. 4 shows (A) the relationship between urine IPG P-type and protein in urine in pre-eclampsia, (B) the relationship between urine IPG P-type and elevated plasma levels of alanine-aspartate transaminase, and (C) the relationship between urine IPG P-type and platelet counts in pre-eclampsia.
Figure 5A:
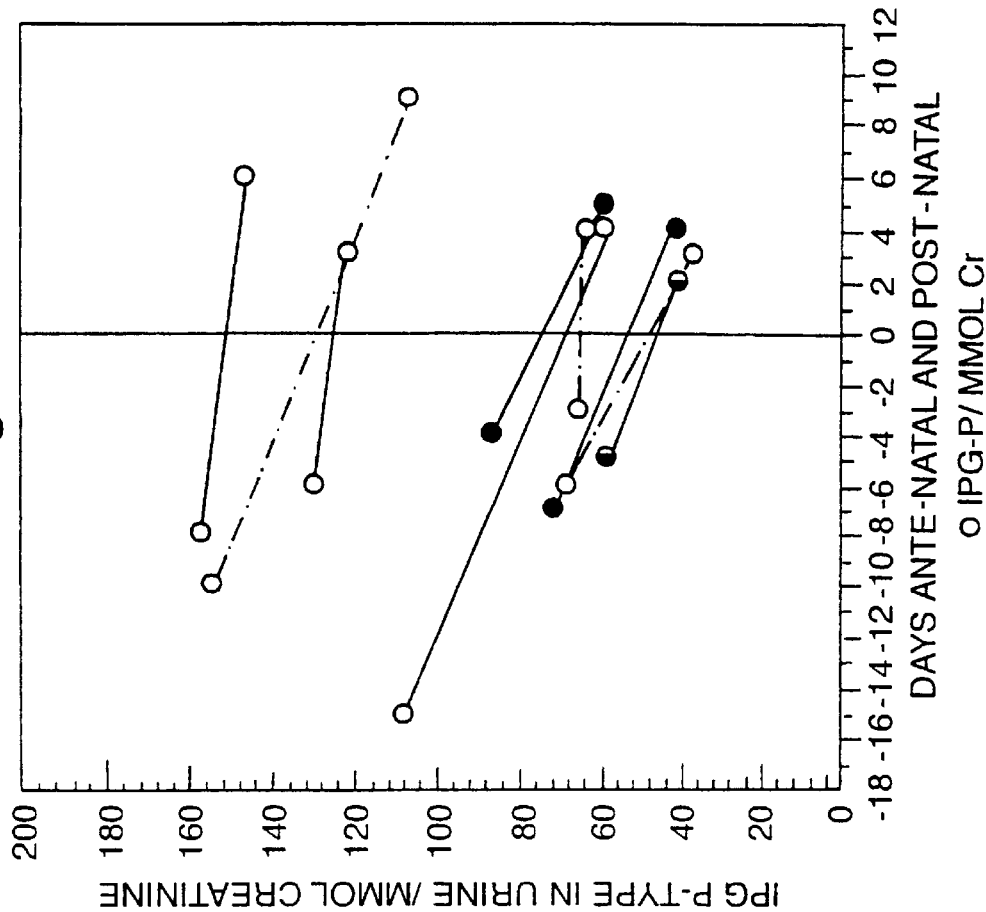
FIG. 5 shows (A) and (B) the concentration of IPG P-type in urine in pre-eclampsia ante-natal and post-natal samples, and (C) urine volumes in pre-eclampsia ante-natal and post-natal samples.
Figure 4C:
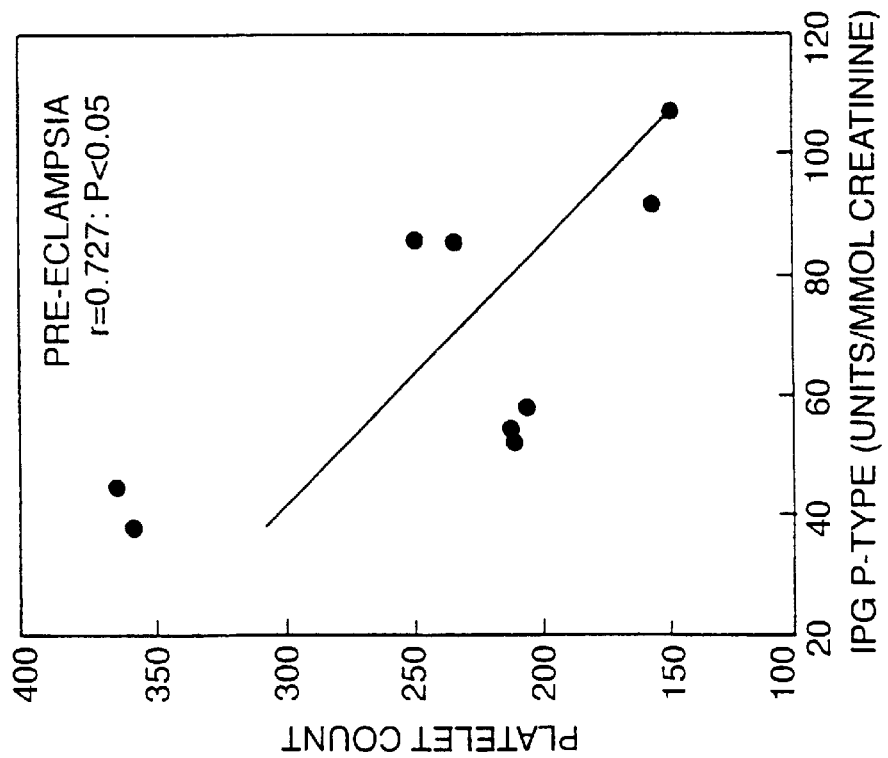
Figure 5C:
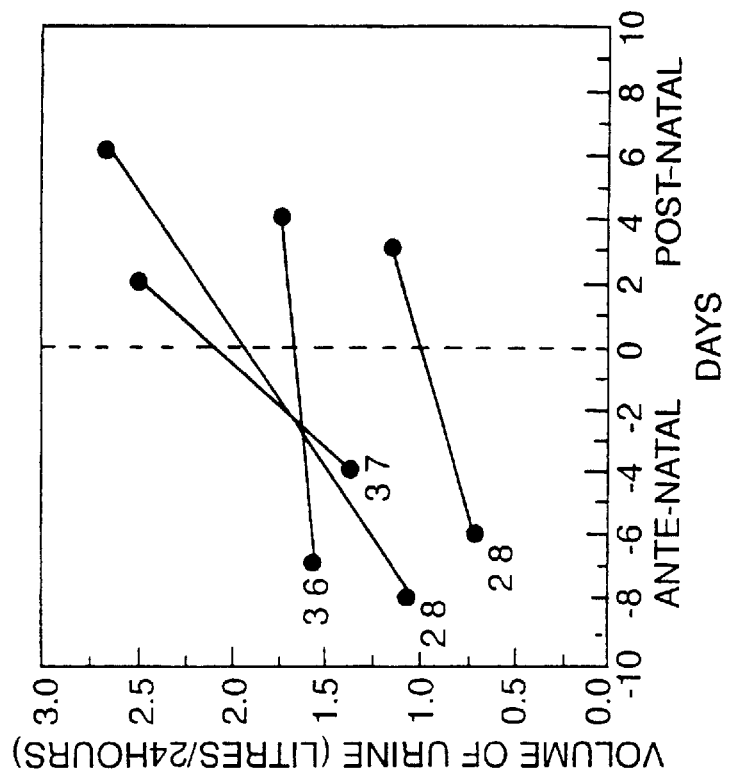
Figure 5B:
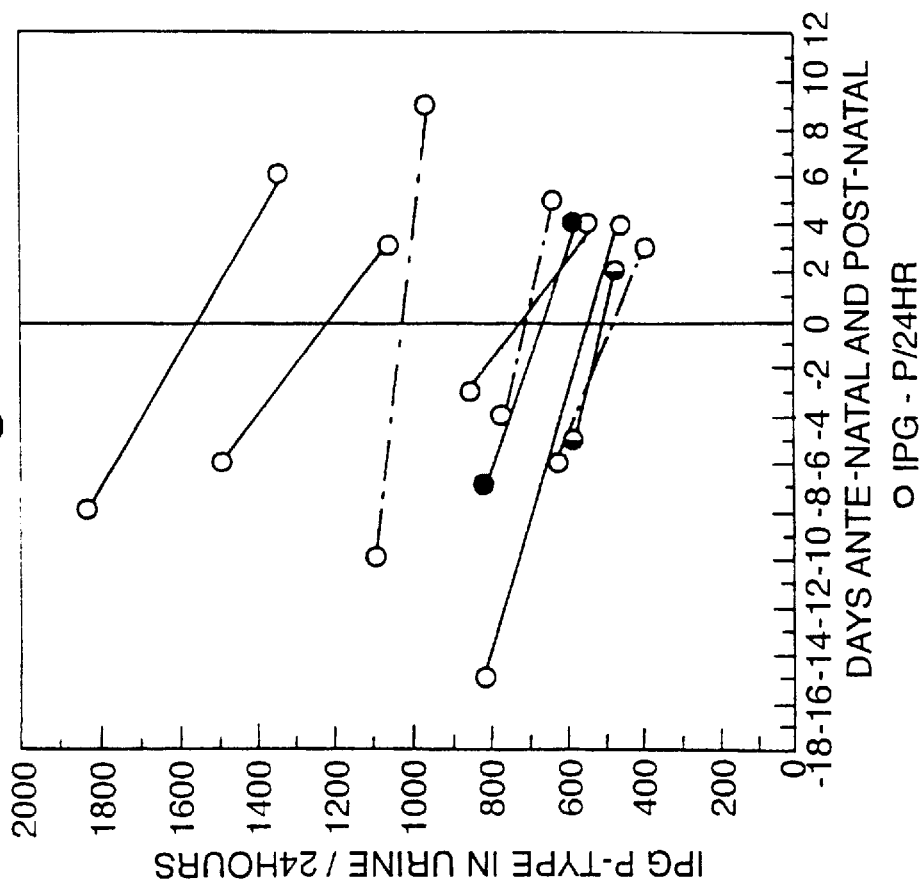

The correlations between these different markers and IPG P-type/mmole creatinine in pre-eclamptic subjects are shown in FIGS. 4 A–C. In summary these results show that:
  (i) Protein in urine—positively correlated with IPG P-type, P<0.01.
  (ii) Alanine—aspartate transaminase—positively correlated, P<0.05.
  (iii) Platelet count—negatively correlated with IPG P-type, P<0.05.

6.2 IPG A-type and Markers of Pre-eclampsia:

It was noted, in Table 2, that IPG A-type showed an upward trend in pre-eclamptic subjects although this was only significant on the basis of IPG A-type/mmol creatinine and was less marked than the IPG P-type. While the present relatively small differences in a sample of ten subjects makes conclusions drawn from these results only tentative, it was found that there was a positive correlation between increased IPG A-type and systolic blood pressure (P<0.05). This observation is, perhaps, strengthened by the parallel correlation found in a separate study of 31 diabetic male subjects in which there was a clear positive correlation between IPG A-type and raised blood pressure. However, it is probable that rigorous control of blood pressure would be maintained in all pre-eclamptic subjects, masking possible underlying links between IPGs and blood pressure in the present study.

C. Discussion

The possibility that inositol phosphoglycans may be particularly important as part of the signal transduction system in placenta in regulating glucose and glycogen metabolism and steroidogenesis stems from the evidence that:
  (i) Insulin mediators of this class can be isolated from placental plasma membranes [22] and from freeze-clamped intact placental tissue (Table 1);
  (ii) IPG P-type activates glycogen synthase phosphatase and pyruvate dehydrogenase phosphatase [6, 7, 11, 17];
  (iii) Inositol phosphoglycans have been shown to be a signal transduction system in the regulation of human placental steroidogenesis [16, 23].

The present results show clearly that the human placenta is a particularly rich source of IPG P-type and differences between non-pregnant and pregnant groups provides strong evidence that the rise in urinary content in normal pregnancy and in pre-eclampsia originates from the placenta. This was confirmed by direct analysis of placenta samples. The highly significant two- to three-fold rise in IPG P-type in urine of the pre-eclamptic group, over and above the matched control group, a difference that is even more significant at earlier stages of pregnancy (FIG. 3A), has been shown to correlate with markers of pre-eclampsia (FIGS. 4 A–C). Further, the elevated IPG P-type provides an explanation for the striking accumulation of glycogen in the placenta in pre-eclampsia (Scheme 1).

It is postulated that different mechanisms are involved in the glycogen accumulation in the placenta in pre-eclampsia and diabetes (see Scheme 1). In contrast to pre-eclampsia, there is no evidence for a rise in IPG P-type in the urine in pregnant diabetic subjects relative to their matched controls (Table 2) and in this condition the increased accumulation of glycogen may relate to the increases in glucose and glucose 6-phosphate in this tissue as shown by Shafrir et. al [5, 24]. As pointed out by these authors, both glucose and glucose 6-phosphate are activators of glycogen synthase, the raised accumulation of glycogen thus relates to the maternal hyperglycaemia. In this regard, the placenta in diabetes shows certain parallelisms to the response of the kidney in diabetes, the latter has a raised glucose and glucose 6-phosphate content and also accumulates glycogen. Thus, both tissues exhibit features of glucose over-utilization in diabetes [25].

While the present results show a close association between markers of pre-eclampsia and the concentration and daily excretion of IPG P-type we do not know whether this is 'cause' or 'effect'. It is likely that the circulating concentration of IPG P- type in the plasma is also increased in pre-eclampsia. Should experimental data confirm this assumption, the question can then be asked as to whether the raised circulating level of a mediator, which can activate both paracrine and autocrine signalling systems, might affect the functions of other tissues and endocrine organs.

The exposure of endothelial cells, widely thought to be dysfunctional in pre-eclampsia [3], to raised levels of IPG P-type, might be critical in the link between IPG P-type production in the placenta and systemic effects. The inositol phosphoglycans appear to have autocrine and paracrine regulatory functions affecting placental steroidogenesis [16], insulin-dependent progesterone synthesis in swine ovary granulosa cells [23], FSH and HCG stimulus of granulosa cells [26]. ACTH signalling of bovine adrenal cells [27], TSH stimulation of thyroid cells [28], IGF1 stimulation of BALB/C3T3 granulosa cells [29], transforming growth factor B on chondrocytes [30], and activation of human platelets [31].

A particularly interesting facet of the present study is the apparent absence of extractable IPG A-type from six different placentae and from multiple samples from a single placenta (Table 1). A number of explanations can be put forward. It may be that IPG A-type decreases markedly in the third trimester, that it is less stable in the placenta after birth and before freezing and extraction, that it has a hgih degree of tissue specificity and is not active in the adipocyte assay system or, more interestingly, that it is, indeed, markedly low in the placenta. In contradistinction to IPG P-type, the enzymes affected by IPG A-type include a number centering upon regulation of protein phosphorylation, these include: inhibition of adenylate cyclase and cAMP dependent protein kinase and activation of a membrane bound low Km cAMP phosphodiesterase [6, 7].

It could be argued that placenta is essentially a unidirectional system, transferring nutrients from the maternal to the fetal circulation and acting as a buffering system for glucose in the storage and release of glycogen. The on/off and the biosynthetic/degradation cycles regulated by protein phosphorylation cycles seen in liver (glycolysis/gluconeogenesis) and adipose tissue (lipogenesis/lipolysis) do not appear to play a major role in placental function [18–20]. Further work is needed in this aspect of regulation of placental metabolism better to define the regulation of the synthesis and the role of inositol phosphoglycans.

The new findings of increased excretion of IPG P-type in urine, and the possibility that it originates in the placenta in pre-eclampsia, suggests a mechanism for the accumulation of glycogen in the syncytiotrophoblast of pre-eclamptic pregnancies. The correlation of these changes in IPG P-type with the markers of the severity of the syndrome of pre-eclampsia also suggests that at least part of this dysfunction may arise from excessive levels of the signalling system.

TABLE 1

Yields of IPG P-type and IPG A-type from placenta and liver

| | Wt taken (g) | Calculated Units/(g) IPG P-type (pH 2.0) | | Wt taken (g) | Calculated Units/g IPG P-type (pH 2.0) | Calculated Units/g IPG P A-type (pH 1.3) |
|---|---|---|---|---|---|---|
| PRE-ECLAMPTIC Human placenta | | | CONTROL | | | |
| Placenta No | | | Placenta No | | | |
| PE1JB | 0.18 | 581 | Con 8CA | 0.34 | 266 | ND |
| | 0.26 | 522 | | 0.49 | 159 | ND |
| | 0.47 | 242 | | 1.05 | 47 | ND |
| | 1.03 | 81 | | | | |
| Human Liver (n = 2) | | | | | 1.82 | 1.60 |
| Rat Liver (n = 13) | | | | | 2.60 ± 0.22 | 2.6 ± 0.12 |

ND—none detected

TABLE 2

The concentration and total daily output of inositol phosphoglycans in the urine of pre-eclamptic, or pregnant diabetic and matched control subjects and a non-pregnant control group.

|  | Stimulation 10 µl urine | IPG P-Type Units/mmol creatinine | 24 daily output (units) | Stimulation 10 µl urine | IPG A-Type Units/mmol creatinine | 24 hour daily output (units) | Creatinine (mmol/L) |
|---|---|---|---|---|---|---|---|
| PRE-ECLAMPTIC GROUP | | | | | | | |
| CONTROLS (n = 10) | 94.1 ± 11.1 | 30.5 ± 8.94 | 316 ± 62 | 81.4 ± 8.4 | 25.9 ± 3.48 | 251 ± 42 | 6.94 ± 0.90 |
| PRE-ECLAMPSIA (n = 10) | 205 ± 43** | 96.4 ± 29.2** | 854 ± 318** | 102 ± 8.4 | 48.5 ± 6.98** | 407 ± 78 | 4.79 ± 0.58 |
| PREGNANT DIABETIC GROUP | | | | | | | |
| CONTROLS (n = 10) | 129 ± 26 | 38.5 ± 5.12 | 374 ± 47 | 84.5 ± 13.5 | 29.2 ± 5.5 | 294 ± 57 | 6.41 ± 0.53 |
| DIABETICS (n = 10) | 89.8 ± 11.0 | 37.3 ± 7.64 | 275 ± 48 | 82.1 ± 9.4 | 34.6 ± 8.12 | 253 ± 45 | 5.94 ± 0.76 |
| NON-PREGNANT GROUP | | | | | | | |
| (n = 10) | 68.2 ± 12.3 | 18.8 ± 1.98 | 187 ± 25 | 97.8 ± 11.8 | 32.7 ± 6.02 | 346 ± 75 | 7.11 ± 0.81 |

The results are given as Means ± SEM for 10 subjects in each group. The control subjects for the pre-eclamptic and diabetic groups were matched for gestational stage, parity and age; a normal non-pregnant group is shown. The data are given as the percentage stimulation of pyruvate dehydrogenase phosphatase (IPG P-type) or percentage stimulation of lipogenesis (IPG A-type) (i) per unit volume of urine (10 µl = 10 ml urine); (ii) as units of IPG activity/mmol creatinine or (iii) as total 24 hour output of units of IPG activity. 1 unit is defined as the amount of IPG causing a 50% increase in bioassay system.
The statistical significance was assessed by the Mann-Whitney test
*P, <0.05:
**P, <0.01

TABLE 3

Calculation of the placental contribution to the amount of IPG P-type found in the urine of pregnant women, including diabetic, pre-eclamptic (PET) and their matched control groups.

| GROUP | IPG P-TYPE (units/mmol creatinine) | DIFFERENCES BETWEEN PREGNANT AND NON-PREGNANT GROUPS |
|---|---|---|
| Non-pregnant group | 18.8 ± 1.98 | — |
| Pregnant groups | | |
| Diabetic group | | |
| Controls | 38.5 ± 5.12 | +19.7 ± 5.12 |
| Diabetics | 37.3 ± 7.64 | +18.5 ± 7.64 |
| Ratio D/C | 0.97 | 0.94 |
| Pre-eclamptic group | | |
| Controls | 30.5 ± 8.94 | +11.7 ± 8.94 |
| Pre-eclampsia | 96.4 ± 29.2 | +77.6 ± 29.2 |
| Ratio PET/C | 3.2 | 6.6 |

Calculated from data in Table 2. Each group contained 10 values; the results are given as means ±SEM.

TABLE 4

The IPG P-type and IPG A-type content of urines from normal non-pregnant female subjects and from normal male subjects.

|  | IPG P-type | IPG A-type | IPG P IPA A |
|---|---|---|---|
|  | Units/mmol creatinine | | |
| Females (10) No treatment | 18.8 ± 1.98 16.1 ± 2.14 | 32.7 ± 6.02 29.5 ± 6.02 | 0.57 |

TABLE 4-continued

The IPG P-type and IPG A-type content of urines from normal non-pregnant female subjects and from normal male subjects.

|  | IPG P-type | IPG A-type | IPG P IPA A |
|---|---|---|---|
|  | Units/mmol creatinine | | |
| (5) | 21.5 ± 3.01 | 43.4 ± 10.5 | |
| Males (27) | 19.3 ± 1.8 | 6.30 ± 0.78 | 3.06 |
| P value, female v male | NS | <0.001 | |

Values for males are taken from a separate survey of IPA A- and IPG P-types in the urine of diabetic and control male subjects.

TABLE 5

IPG P-type in human placenta and urine in pre-eclamptic and normal pregnant subjects.

|  | Pre-eclamptic | Control | PE/C |
|---|---|---|---|
| Placenta [1] | Units/g | Units/g | |
| IPG P-type | 81 ± 11 (5) | 30 ± 6 (4)** | 2.7 |
| Urine [2] | Units/24 h | Units/24 h | |
| IPG P-type | 854 ± 318 (10) | 316 ± 62 (10)** | 2.7 |

[1] Non-matched samples of placenta
[2] Urine samples matched for gestational age and parity
IPG P-type activates pryuvate dehydrogenase phosphatase and glycogen synthase phosphatase.
A unit of IPG P-type activity is defined as the amount producing a 50% stimulation of PDH phosphatase.
Values are the means ± SEM; Fisher's P values shown by **P < 0.01.

TABLE 6

Placental Glycogen content & glycogen synthase activity [3].

| Pre-eclamptic | Control | PE/C |
|---|---|---|
| Chorionic villi - glycogen content ug/g tissue) | | |
| 1300 | 570 | 2.3 |
| STB microvesicles - glycogen content (ug/mg protein) | | |
| 223 | 25 | 9.7 |
| STB micro vesicles-glycogen synthase (units/mg protein) | | |
| 1323 | 83 | 16 |

[3] Data from: Arkwright, Rolemaker, Dwek, Redman 1993) J Clin Invest 91:2744–2753

TABLE 7

IPG CONTENT OF PRE-ECLAMPTIC URINES ANTE-v POST-NATAL

| State | Creatinine mmol/L | Units/L urine | Units/mmol creatinine | Total excretion |
|---|---|---|---|---|
| IPG P-TYPE | | | | |
| Ante- | 6.58 ± 0.86 | 632 ± 112 | 98.9 ± 12.1 | 850 ± 105 |
| Post- | 5.78 ± 0.64 | 406 ± 51 | 70.8 ± 12.2 | 747 ± 127 |
| Paired t | NS | NS | ** | ** |
| IPG A-TYPE | | | | |
| Ante- | | 149 ± 23.2 | 26.2 ± 5.6 | 234 ± 60 |
| Post- | | 148 ± 19.2 | 30.4 ± 6.5 | 286 ± 66 |
| Paired t | | NS | NS | NS | n = 9

References

The references mentioned herein are all expressly incorporated by reference.

1. Redman, C. W. G., 1991. Current topic: pre-eclampsia and the placenta. Placenta, 12: 301–308.
2. Robertson, W. B., Brosens, I. A. and Dixon, H. G. 1967. The pathological response of the vessels of the placental bed to hypertensive pregnancy. J. Path. Bacteriol. 93; 581–592.
3. Roberts, J. M., Taylor, R. N., Musci, T. J., Rodgers, G. M., Hubel, C. A. and McLaughlin, M. K. 1989. Pre-eclampsia: an endothelial cell disorder. Am. J. Obstet. Gynecol. 161: 1200–1204.
4. Arkwright, P. D., Rademacher, T. W., Dwek, R. A. and Redman, C. W. 1993. Pre-eclampsia is associated with an increase in trophoblast glycogen content and glycogen synthase activity similar to that found in hydatiform mole. J. Clin. Invest. 91: 2744–2753.
5. Shafrir. E. and Barash, V. 1991. Placental glycogen metabolism in diabetic pregnancy, Isr. J. Med. Sci. 27: 449–461.
6. Romero, G. 1991. Inositol glycans and cellular signalling. Cell Biol. International Rev. 15: 827–851.
7. Romero. G. and Larner, J. 1993. Insulin mediators and the mechanism of insulin action. Adv. Pharmacol. 28: 21–50.
8. Rademacher, T. W., Caro, H. N., Kunjara, S., Wang, D. Y., Greenbaum, A. L. and McLean, P. 1994. Inositolphosphoglycan second messengers. Brazilian J. Med. Biol. Res. 27: 327–341.
9. Kunjara, S., Caro, H. N., McLean, P. and Rademacher, T. W. 1995. Tissue specific release of inositol phosphoglycans. In Svasti, J. et. al. (Eds). Biopolymers and bioproducts: Structure, function and applications. Bangkok, Thailand. Samakkhisan (Dokya). Public Co. Ltd. pp 301–306.
10. Kaaja, R., Tikkanen, M. J., Vinikka, L. and Ylikorkala, O. 1995. Serun lipoproteins, insulin and urinary prostanoid metabolites in normal and hypertensive pregnant women. Obstet. Gynecol. 85: 353–356.
11. Lilley, K., Zhang, C., Villar-Palasi, C., Larner, J. and Huang, L. 1992. Insulin mediator stimulation of pyruvate dehydrogenase phosphatase. Arch. Biochem. Biophys. 296: 170–174.
12. Larner, J., Huang, L. C., Suzuki, S., Tang, E., Zhang, C., Schwartz, C. F. W., Romero, G., Luttrell, L. And Kennington, A. S. 1989. Insulin mediators and the control of pyruvate dehydrogenase complex. Annals N. Y. Acad. Sci. 573: 297–305.
13. Rodbell, M. 1964. Metabolism of isolated fat cells. J. Biol. chem. 239: 375–380.
14. Newman, J. D., Armstrong, J, McD., and Bornstein, J. 1985. Assay of insulin mediator activity with soluble pyruvate dehydrogenase phosphatase. Endocrinology 116: 1912–1919.
15. Asplin, I., Galasko, G. and Larner, J. 1993. chiro-Inositol deficiency and insulin resistance: A comparison of the chiro-inositol- and the myo-inositol-containing insulin mediators isolated from urine, hemodialysate; and muscle of control and type II diabetic subject. Proc. Natl. Acad. Saa USA 90-: 5924–5923.
16. Nestler, J. E., Romero. G., Huang, L., Zhang, C., and Larner, J. 1991. Insulin mediators are the signal transduction system responsible for insulin action on human placental steroidogenesis. Endocrinology 129: 2951–2956. 17. Lazar, D. F., Knez, J. J., Medof, E., Cuatracasas, P. and Saltiel, A. R. 1994. Stimulation of glycogen synthesis by insulin in human erythroleukemia cells requires the synthesis of glycosyl-phosphatidyl inositol, Proc. Natl. Acad. Sci. USA. 91: 9665–9669.
18. Diamant, Y. Z., Mayorek, N, Neumann, S. and Shafrir, E. 1975. Enzymes of glucose and fatty acid metabolism in early and term human placenta. Amer. J. Obstet. Gynecol. 121: 58–61.
19. Diamant, Y. Z., Beyth, Y., Neumann, S. and Shafrir, E. 1976. Activity of placental enzymes of carbohydrate and lipid metabolism in normal, toxaemic and small-for-date pregnancies. Isr. J. Med. Sci. 12: 243–247.
20. Shafrir, E. and Diamant, Y. Z. 1978. Regulation of placental enzymes of carbohydrate and lipid metabolic pathways. Ciba Foundation Symposium 63: 161–179.
21. Redline, R. W., and Petterson, P. 1995. Pre-eclampsia is associated with an excess of proliferative immature intermediate trophoblast. Human Pathol. 26: 594–600.
22. Suzuki, S., Toyota, T., Suzuki, K., and Goto, Y. 1984. Partial purification form human mononuclear cells and placental membranes of an insulin mediator which stimulates pyruvate dehydrogenase and suppresses glucose 6-phosphatase. Arch. Biochem. Biophys. 235: 418–426.
23. Romero, G., Garmey, J. C., Velduis, J. D. 1993. The involvement of inositol phosphoglycan mediators in the modulation of steroidogenesis by insulin and insulin-like growth factor-1. Endocrinology, 132: 1561–1568.
24. Barash. B., Gutman, A., and Shafrir, E. 1983. Mechanism of placental glycogen deposition in diabetes in the rat. Diabetologia, 24: 63–68.
25. Sochor, T., Baquer, N. Z., and McLean, P. 1985. Glucose over-and under-utilization in diabetes. Comparative studies in changes of activities of enzymes of glucose metabolism in rat kidney and liver. Molecular Physiol. 2: 51–68.

26. Fanjul, L. F., Marrero, I., Estevez, F., Gonzalez, J., Quintana, J., Santana, P., and Ruiz de Galarreta C. M. 1993. Follicle-stimulating hormone and human chorionic gonadotrophin induced changes in granulosa cell glycosyl-phosphatidylinositol concentration. J. Cell. Physiol. 155:273–281.
27. Igarashi, Y., and Chambaz, E. M. 1987. A novel inositol phospholipid and the serum dependence of its metabolism in bovine adrenocortical cells. Biochem Biophys. Res. Commun. 145: 248–256.
28. Martiny, L., Antonicelli, F., Thuilliez, B., Lambert, B., Jaquemin, C., and Haye, B. 1990. Control by thyrotropin of the production by thyroid cells of an inositol phosphate-glycan. Cell Signalling, 2: 21–27.
29. Kojima, I., Kitaoka, M., and Ogata, E. 1990. Insulin-like growth factor-1 stimulates diacylglycerol production via multiple pathways in BALB/c 3T3 cells. J. Biol. Chem. 265: 16846–16850.
30. Vivien. D., Petitfrere, E., Martiny, L., Sartelet, H., Galera, P., Hate, B., and Pujol, J-P 1993. IPG (inositolphosphate glycan) as a cellular signal for TGF-B1 modulation of chondrocyte cell cycle. J. Cellular Physiol. 155: 437–444.
31. Bruni, P., Vasta, V., Berti, L., Avila, M. A., Farnararo, M., Varela-Nieto, I. 1991. An inositol phosphoglycan stimulates glycolysis in human platelets. Biochem. Biophys. Res. Commun. 180: 1041–1047.

What is claimed is:

1. A method of diagnosing pre-eclampsia in a patient, the method comprising determining the level of P-type IPGs in a biological sample obtained from the patient, wherein an elevated level of P-type IPGs, as compared to a control level, is indicative of pre-eclampsia or risk for pre-eclampsia, wherein the level of P-type IPGs is determined using an assay selected from the group consisting of:

(i) measurement of activation of pyruvate dehydrogenase phosphatase;
   (ii) measurement of activation of glycogen synthetase phosphatase; and
   (iii) an immunoassay.

2. The method of claim 1 wherein the level of the P-type IPGs is determined using an assay measuring activation of glycogen synthetase phosphatase by P-type IPGs.

3. The method of claim 1 wherein the level of the P-type IPGs is determined in an assay measuring activation of pyruvate dehydrogenase phosphatase by P-type IPGs.

4. The method of claim 1 wherein the level of the P-type IPGs is determined using an immunoassay.

5. The method of claim 4, the method comprising:
   (a) contacting a biological sample obtained from the patient with a solid support having immobilized thereon antibody having one or more binding sites specific for one or more P-type IPGs;
   (b) contacting the solid support with a labelled developing agent capable of binding to P-type IPG's bound to antibodies or capable of binding to anti-P-type IPG antibodies; and
   (c) detecting the label of the developing agent specifically binding in (b) to obtain a value representative of the level of the P-type IPGs in the sample.

6. The method of claim 1 wherein an elevated level of the P-type IPGs is greater than about 2 times the level in control subjects.

7. The method of claim 1 wherein the sample is a blood, serum, tissue or urine sample.

8. The method of claim 2 wherein an elevated level of the P-type IPGs is greater than about 2 times the level in control subjects.

9. The method of claim 3 wherein an elevated level of the P-type IPGs is greater than about 2 times the level in control subjects.

10. The method of claim 4 wherein an elevated level of the P-type IPGs is greater than about 2 times the level in control subjects.

11. The method of claim 4 wherein the sample is a blood, serum, tissue or urine sample.

12. The method of claim 5 wherein an elevated level of the P-type IPGs is greater than about 2 times the level in control subjects.

13. The method of claim 5 wherein the sample is a blood, serum, tissue or urine sample.

14. The method of claim 5 wherein the labelled developing agent is capable of binding to bound P-type IPGs.

15. A method of diagnosing pre-eclampsia in a patient, the method comprising determining the level of P-type IPGs in a biological sample obtained from the patient, wherein said P-type IPGs are capable of activating pyruvate dehydrogenase phosphatase, and a P-type IPG level elevated by more than about 2-fold, as compared to a control level, is indicative of pre-eclampsia or risk for pre-eclampsia, wherein the level of P-type IPGs is determined using an immunoassay.

16. The method of claim 15 wherein the sample is a blood, serum, tissue or urine sample.

17. The method of claim 16, the method comprising:
   (a) contacting the sample with a solid support having an anti-P-type IPG antibody immobilized thereon;
   (b) contacting the solid support with a labelled developing agent capable of binding to P-type IPG's bound to antibodies or capable of binding to anti-P-type IPG antibodies; and
   (c) detecting the label of the developing agent specifically binding in (b) to obtain a value representative of the level of the P-type IPGs in the sample.

18. The method of claim 17 wherein (i) the immobilized antibody comprises a monoclonal antibody, (ii) after contact with the sample, the solid support is contacted with a polyclonal antibody capable of specifically binding to IPGs, and (iii) the developing agent comprises an antibody capable of specifically binding to the polyclonal antibody.

* * * * *